(12) United States Patent
Ambrose et al.

(10) Patent No.: US 7,700,317 B2
(45) Date of Patent: Apr. 20, 2010

(54) TRUNCATED BAFF RECEPTORS

(75) Inventors: Christine Ambrose, Reading, MA (US); Jeffrey Thompson, Stoneham, MA (US); Yen-Ming Hsu, Lexington, MA (US); Dingyi Wen, Waltham, MA (US); Yaping Sun, Lexington, MA (US)

(73) Assignee: Biogen Idec Ma Inc., Cambridge, MA (US)

( * ) Notice: Subject to any disclaimer, the term of this patent is extended or adjusted under 35 U.S.C. 154(b) by 913 days.

(21) Appl. No.: 10/550,961

(22) PCT Filed: Mar. 26, 2004

(86) PCT No.: PCT/US2004/007692

§ 371 (c)(1),
(2), (4) Date: May 17, 2006

(87) PCT Pub. No.: WO2004/094620

PCT Pub. Date: Nov. 4, 2004

(65) Prior Publication Data

US 2006/0234917 A1    Oct. 19, 2006

Related U.S. Application Data

(60) Provisional application No. 60/458,707, filed on Mar. 28, 2003.

(51) Int. Cl.
| | |
|---|---|
| C12P 21/00 | (2006.01) |
| C12N 5/00 | (2006.01) |
| C12N 1/20 | (2006.01) |
| C12N 15/00 | (2006.01) |
| A61K 38/17 | (2006.01) |
| C07K 14/705 | (2006.01) |
| C07H 21/04 | (2006.01) |

(52) U.S. Cl. .................. 435/69.1; 435/70.1; 435/252.3; 435/320.1; 435/325; 424/184.1; 424/185.1; 424/134.1; 514/12; 530/300; 530/350; 536/23.1

(58) Field of Classification Search ........................ None
See application file for complete search history.

(56) References Cited

U.S. PATENT DOCUMENTS

| | | | |
|---|---|---|---|
| 5,595,721 | A | 1/1997 | Kaminski et al. |
| 5,969,102 | A | 10/1999 | Bram et al. |
| 6,297,367 | B1 | 10/2001 | Tribouley |
| 6,316,222 | B1 | 11/2001 | Bram et al. |
| 6,403,770 | B1 | 6/2002 | Yu et al. |
| 6,475,986 | B1 | 11/2002 | Aggarwal |
| 6,475,987 | B1 | 11/2002 | Shu |
| 6,541,224 | B2 | 4/2003 | Yu et al. |
| 6,551,795 | B1 | 4/2003 | Rubenfield et al. |
| 6,623,941 | B1 | 9/2003 | Ruben et al. |
| 6,689,579 | B1 | 2/2004 | Yu et al. |
| 2002/0037852 | A1 | 3/2002 | Browing et al. |
| 2002/0165156 | A1 | 11/2002 | Browing et al. |
| 2002/0172674 | A1 | 11/2002 | Browing et al. |
| 2003/0023038 | A1 | 1/2003 | Rennert et al. |
| 2003/0082175 | A1 | 5/2003 | Schneider et al. |
| 2003/0092164 | A1 | 5/2003 | Gross et al. |
| 2003/0095967 | A1 | 5/2003 | MacKay et al. |
| 2003/0194743 | A1 | 10/2003 | Beltzer et al. |

FOREIGN PATENT DOCUMENTS

| | | |
|---|---|---|
| EP | 0 869 180 A1 | 10/1998 |
| WO | WO 97/33902 | 9/1997 |
| WO | WO 98/18921 | 5/1998 |
| WO | WO 98/27114 | 6/1998 |
| WO | WO 98/39361 | 9/1998 |
| WO | WO 98/55620 | 12/1998 |
| WO | WO 98/55621 | 12/1998 |
| WO | WO 99/04001 | 1/1999 |
| WO | WO 99/11791 | 3/1999 |
| WO | WO 99/12964 | 3/1999 |
| WO | WO 99/12965 | 3/1999 |
| WO | WO 99/33980 | 7/1999 |
| WO | WO 00/26244 | 5/2000 |
| WO | WO 00/39295 | 7/2000 |
| WO | WO 00/40716 | 7/2000 |
| WO | WO 00/43032 | 7/2000 |
| WO | WO 00/50597 | 8/2000 |
| WO | WO 00/50633 | 8/2000 |
| WO | WO 00/58362 | 10/2000 |
| WO | WO 01/12812 | 2/2001 |

(Continued)

OTHER PUBLICATIONS

Kalled et al. BAFF: B cell survival factor and emerging therapeutic target for autoimmune disorders. Expert Opin Ther Targets 7(1):115-123, 2003.*

(Continued)

*Primary Examiner*—Bridget E Bunner
(74) *Attorney, Agent, or Firm*—Finnegan, Henderson, Farabow, Garrett & Dunner, LLP

(57) ABSTRACT

The disclosure provides a non-naturally occurring BAFF-R glycoprotein having a deletion in the extracellular domain which results in an altered O-linked glycosylation pattern. The disclosure also provides methods and pharmaceutical compositions for treating B-cell- and T-cell-mediated disorders.

43 Claims, 19 Drawing Sheets

FOREIGN PATENT DOCUMENTS

| WO | WO 01/24811 | 4/2001 |
|---|---|---|
| WO | WO 02/02641 | 1/2002 |
| WO | WO 02/18620 | 3/2002 |
| WO | WO 02/24909 | 3/2002 |
| WO | WO 02/38766 | 5/2002 |
| WO | WO 02/092620 | 11/2002 |
| WO | WO 03/014294 | 2/2003 |
| WO | WO 03/024991 | 3/2003 |
| WO | WO 03/035846 | 5/2003 |
| WO | WO 03/055979 | 7/2003 |
| WO | WO 2004/035735 | 4/2004 |
| WO | WO 2005/005462 | 1/2005 |

OTHER PUBLICATIONS

Tangye et al. BAFF, April, and human B cell disorders. Seminars Immunol 18(5): 305-317, 2005.*

Schneider et al. BAFF and the regulation of B cell survival. Immunol Lett 88: 57-62, 2003.*

Wells. J.A. Additivity of mutational effects in proteins. Biochemistry 29 (37): 8509-8517, 1990.*

Ngo et al. Computational complexity, protein structure prediction, and the Levinthal paradox. The Protein Folding Problem and Tertiary Structure Prediction, pp. 492-495, 1994.*

Phillips, AJ. The challenge of gene therapy and DNA delivery. J Pharm Pharmacol 53: 1169-1174, 2001.*

Database Accession No. AI250289, XP002206618, Dec. 23, 1998.

Database Accession No. Z99716.4, XP002206619, Dec. 14, 1999.

Do et al., "Attenuation of apoptosis underlies B Lymphocyte stimulator enhancement of humoral immune response," *J. Exp. Med.* 192(7):953-964 (2000).

Domingues, H.M., "Rational design strategies to improve cytokine foldability and minimization of a functional motif: The IL-4 Case," *Thesis University of Utrecht*, p. 48, line 25—p. 51, line 6, p. 94; table III (1999).

GenBank Accession No. AK008142, Published Feb. 16, 2001.

Gordon et al., "BAFF/BLyS receptor 3 comprises a minimal TNF receptor-like module that encodes a highly focused ligand-binding site," *Biochemistry* 42:5977-5983 (2003).

Gras et al., "BCMAp: An integral membrane protein in the Golgi apparatus of human mature B lymphocytes," *Int. Immunology* 7(7):1093-1106 (1995).

Gross et al., "TACI and BCMA are receptors for a TNF homologue implicated in B-Cell autoimmune disease," *Nature*, 404:995-999 (2000).

Hahne et al., "APRIL, a new ligand of the tumor necrosis family, stimulates tumor cell growth," *J. Exp. Med* 188(6):1185-1190 (1998).

Kashii, Y. et al., "Constitutive expression and role of the family ligands in apoptotic killing of tumor cells by human NK cells," *J. Immunol.* 163:5358-66 (1999).

Kayagaki et al. "BAFF/BLyS receptor 3 binds the B Cell survival factor BAFF ligand through a discrete surface loop and promotes processing of NF-$_k$ B2, " *Immunity* 10:515-524 (2002).

Khare et al., "The role of TALL-1 and APRIL in immune regulations," *Trends Immunol.* 22(2):61-63 (2001).

Khare et al., "Severe B cell hyperplasia and autoimmune disease in TALL-1 transgenic mice," *PNAS* 97(7):3370-3375 (2000).

Kwon et al., "Single amino acid substitutions of $\alpha_1$—Antitrypsin that confer enhancement in thermal stability," *J. Biol. Chem.*, 269:9627-9631 (1994).

Laabi et al., "A BCMA gene, preferentially expressed during B lymphoid maturation, 13 bidirectionally transcribed," *Nucleic Acids Res.* 22(7):1147-1154 (1994).

Laabi et al., "The new gene, BCM, on chromosome 16 is fused to the interleukin 2 gene by a t(4;16)(q26,p13) translocation in a malignant T cell lymphoma," *EMBO J.* 11:3897-3904 (1992).

Mackay et al., "Mice transgenic for BAFF develop lymphocyte disorders along with autoimmune manifestations," *J. Exp. Med* 190(11):1697-1710 (1999).

Madry et al., "The characterization of murine BCMA gene defines it as a new member of the tumor necrosis factor receptor superfamily," *Int. Immunol.* 10(11):1693-1702 (1998).

Marsters et al., "Interaction of the TNF homologues BLyS and APRIL with the TNF receptor homologues BCMA and TACI," *Curr. Biol.*, 10:785-788 (2000).

Moore et al., "BlyS, Member of the tumor necrosis factor family and B lymphocyte stimulator," *Science* 282:260-263 (1999).

Schein, C.H., "Production of soluble recombinant proteins in bacteria," *Biotechnology*, 7:1141-1149 (1989).

Schiemann et al., "An essential role for BAFF in the normal development of B Cells through a BCMA-independent pathway," *Science*, 293:2111-2114 (2001).

Schneider et al., "BAFF, a novel ligand of the tumor necrosis factor family, stimulates B cell growth," *J. Exp. Med.*, 189:1747-1756 (1999).

Shu et al., "TALL-1 is a novel member of the TNF family that is down-regulated by mitogens," *J. Leukocyte Biol.* 65:680-683 (1999).

Thompson et al., "BAFF binds to the tumor necrosis factor receptor-like molecule B Cell maturation antigen and is important for maintaining the peripheral B Cell population," *J. Exp. Med*, 192:129-135 (2000).

Thompson et al., "BAFF-R, a newly identified TNF Receptor that specifically interacts with BAFF," *Science*, 293:2108-2111 (2001).

von Bulow & Bram, "NT-AT activation induced by a CAML-interacting member of the tumor necrosis factor receptor superfamily," *Science* 278:138-141 (1997).

Waldschmidt et al., "Long Live the Mature B-Cell—A baffling mystery resolved," *Science*, 293:2012-2013 (2001).

Ward, P. and Mulligan, M. "Blocking of adhesion molecules in vivo as anti-imflammatory therapy," *Ther. Immunol.* 1:165-71 (1994).

Ware, C., "April and BAFF connect autoimmunity and cancer," *J. Exp. Med.* 192:F35-F37 (2000).

Wood et al., "Prolines and amyloidogenicity in fragments of the Alzheimer's peptide β/A4," *Biochemistry*, 34:724-730 (1995).

Wu et al., "Tumor Necrosis Factor (TNF) receptor superfamily member TACI is a high affinity receptor of TNF family members APRIL and BlyS," *J. Biol. Chem.* 275(45):35478-35485 (2000).

Yan et al., "Identification of a novel receptor for B Lymphocyte stimulator that is mutated in a mouse strain with severe B Cell deficiency," *Curr. Biol.*, 11:1547-1552 (2001).

Yu et al., "APRIL and TALL-1 and receptors BCMA and TACI: System for regulating humoral immunity," *Nature Immunology*, 1:252-256 (2000).

* cited by examiner

1    DVGARRLRVR  SQRSRDSSVP  TQC<u>N</u>QTECFD  PLVRNCVSCE

41   LFHTPDTGHT  SSLEPGTALQ  PQEGSAL (SEQ ID NO:6)

Figure 6A

1    DVRRGPRSLR  GRDAPAPTPC  NPAECFDPLV  RHCVACGLLR

41   <u>T</u>PRPKPAGA<u>S</u>  SPAPR<u>T</u>ALQP  QE<u>S</u>VGAGAGE  A (SEQ ID NO:1)

Figure 6B

```
                        SEQUENCE LISTING

<160> NUMBER OF SEQ ID NOS: 9

<210> SEQ ID NO 1
<211> LENGTH: 72
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: X is V (wild type) or N (substitution)
<220> FEATURE:
<221> NAME/KEY: MISC_FEATURE
<222> LOCATION: (28)..(28)
<223> OTHER INFORMATION: X is L (wild type) or P (substitution)

<400> SEQUENCE: 1

Asp Val Arg Arg Gly Pro Arg Ser Leu Arg Gly Arg Asp Ala Pro Ala
1               5                   10                  15

Pro Thr Pro Cys Xaa Pro Ala Glu Cys Phe Asp Xaa Leu Val Arg His
            20                  25                  30

Cys Val Ala Cys Gly Leu Leu Arg Thr Pro Arg Pro Lys Pro Ala Gly
        35                  40                  45

Ala Ser Ser Pro Ala Pro Arg Thr Ala Leu Gln Pro Gln Glu Ser Val
    50                  55                  60

Gly Ala Gly Ala Gly Glu Ala Ala
65                  70

<210> SEQ ID NO 2
<211> LENGTH: 220
<212> TYPE: DNA
<213> ORGANISM: Homo sapiens

<400> SEQUENCE: 2
gacgtcaggc gagggcccg  gagcctgcgg  ggaagggacg  cgccagcccc  cacgccctgc      60
gtcccggccg  agtgcttcga  cctgctggtc  cgccactgcg  tggcctgcgg  gctcctgcgc     120
acgccgcggc  cgaaaccggc  cggggccagc  agccctgcgc  ccaggacggc  gctgcagccg     180
caggagtcgg  tgggcgcggg  ggccggcgag  gcggcggtcg                              220

<210> SEQ ID NO 3
<211> LENGTH: 220
<212> TYPE: DNA
<213> ORGANISM: Homo sapiens

<400> SEQUENCE: 3
gacgtcaggc  gagggcccg   gagcctgcgg  ggaagggacg  cgccagcccc  cacgccctgc      60
aatccggccg  agtgcttcga  ccctctggtc  cgccactgcg  tggcctgcgg  gctcctgcgc     120
acgccgcggc  cgaaaccggc  cggggccagc  agccctgcgc  ccaggacggc  gctgcagccg     180
caggagtcgg  tgggcgcggg  ggccggcgag  gcggcggtcg                              220
```

<210> SEQ ID NO 4
<211> LENGTH: 227
<212> TYPE: PRT
<213> ORGANISM: Homo sapiens

<400> SEQUENCE: 4

Val Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225

<210> SEQ ID NO 5
<211> LENGTH: 681
<212> TYPE: DNA
<213> ORGANISM: Homo sapiens

<400> SEQUENCE: 5
gtcgacaaaa ctcacacatg cccaccgtgc ccagcacctg aactcctggg gggaccgtca      60
gtcttcctct tccccccaaa acccaaggac accctcatga tctcccggac ccctgaggtc     120
acatgcgtgg tggtggacgt gagccacgaa gaccctgagg tcaagttcaa ctggtacgtg     180
gacggcgtgg aggtgcataa tgccaagaca aagccgcggg aggagcagta caacagcacg     240
taccgtgtgg tcagcgtcct caccgtcctg caccaggact ggctgaatgg caaggagtac     300
aagtgcaagg tctccaacaa agccctccca gcccccatcg agaaaaccat ctccaaagcc     360
aaagggcagc ccgagaacc acaggtgtac accctgcccc catcccggga tgagctgacc      420
aagaaccagg tcagcctgac ctgcctggtc aaaggcttct atcccagcga catcgccgtg     480
gagtgggaga gcaatgggca gccggagaac aactacaaga ccacgcctcc cgtgttggac     540

```
tccgacggct ccttcttcct ctacagcaag ctcaccgtgg acaagagcag gtggcagcag      600
gggaacgtct tctcatgctc cgtgatgcat gaggctctgc acaaccacta cacgcagaag      660
agcctctccc tgtctcccgg g                                                681
```

<210> SEQ ID NO 6
<211> LENGTH: 67
<212> TYPE: PRT
<213> ORGANISM: Mus musculus

<400> SEQUENCE: 6

```
Asp Val Gly Ala Arg Arg Leu Arg Val Arg Ser Gln Arg Ser Arg Asp
1               5                   10                  15

Ser Ser Val Pro Thr Gln Cys Asn Gln Thr Glu Cys Phe Asp Pro Leu
            20                  25                  30

Val Arg Asn Cys Val Ser Cys Glu Leu Phe His Thr Pro Asp Thr Gly
        35                  40                  45

His Thr Ser Ser Leu Glu Pro Gly Thr Ala Leu Gln Pro Gln Glu Gly
    50                  55                  60

Ser Ala Leu
65
```

<210> SEQ ID NO 7
<211> LENGTH: 73
<212> TYPE: PRT
<213> ORGANISM: Homo sapiens
<220> FEATURE:
<221> NAME/KEY: misc_feature
<222> LOCATION: (21)..(21)
<223> OTHER INFORMATION: X is V (wild type) or N (substitution)
<220> FEATURE:
<221> NAME/KEY: misc_feature
<222> LOCATION: (28)..(28)
<223> OTHER INFORMATION: X is L (wild type) or P (substitution)

<400> SEQUENCE: 7

```
Asp Val Arg Arg Gly Pro Arg Ser Leu Arg Gly Arg Asp Ala Pro Ala
1               5                   10                  15

Pro Thr Pro Cys Xaa Pro Ala Glu Cys Phe Asp Xaa Leu Val Arg His
            20                  25                  30

Cys Val Ala Cys Gly Leu Leu Arg Thr Pro Arg Pro Lys Pro Ala Gly
        35                  40                  45

Ala Ala Ser Ser Pro Ala Pro Arg Thr Ala Leu Gln Pro Gln Glu Ser
    50                  55                  60

Val Gly Ala Gly Ala Gly Glu Ala Ala
65                  70
```

<210> SEQ ID NO 8
<211> LENGTH: 56
<212> TYPE: DNA
<213> ORGANISM: Homo sapiens

<400> SEQUENCE: 8

```
tcgaccgccc cggccggttt cggccgcggc gtgcgcagga gcccgcaggc cacgca        56
```

<210> SEQ ID NO 9
<211> LENGTH: 49
<212> TYPE: DNA

-continued

```
<213> ORGANISM: Homo sapiens

<400> SEQUENCE: 9
gtggcctgcg ggctcctgcg cacgccgcgg ccgaaaccgg ccggggcgg                    49
```

TRUNCATED BAFF RECEPTORS

This application claims priority from U.S. Application Ser. No. 60/458,707, filed Mar. 28, 2003, herein incorporated by reference in its entirety.

FIELD OF THE INVENTION

The present disclosure relates to TNF-family ligands and receptors and antagonists and agonists thereof and their use in modulation of immune responses.

BACKGROUND OF THE INVENTION

The present invention relates to the BAFF receptor ("BAFF-R," also known as BR3 and Ztnfr12), a member of the TNF family of receptor proteins. BAFF-R has been described in International Patent Publication WO 02/24909.

BAFF-R specifically binds the TNF family ligand, BAFF (also known as TALL-1, THANK, BLyS, neurokine α, TNSF13B, and zTNF4), which has been described in International Patent Publication WO 00/43032. BAFF enhances B cell survival in vitro (Batten et al. (2000) *J. Exp. Med.* 192 (10): 1453-1466) and has emerged as a key regulator of peripheral B cell populations in vivo. It is believed that abnormally high levels of this ligand may contribute to the pathogenesis of autoimmune diseases by enhancing the survival of autoreactive B cells (Batten et al. (2000) *J. Exp. Med.* 192 (10): 1453-1466). Agonists and antagonists of BAFF activity have been described in WO 00/43032.

Recently, BAFF-specific agents, including BAFF antibodies, have been developed for treatment of autoimmune and other disorders (see, e.g., U.S. patent application Ser. Nos. 09/911,777; 10/380,703; 10/045,574; and 60/512,880); Kalled et al. (2003) *Expert Opin. Ther. Targets,* 7(1):115-23).

Prior to the discovery of BAFF-R, many members of the TNF receptor family had been uncovered by expressed sequence tag (EST) analysis and genomic sequencing. However, some family members, like BAFF-R, required expression cloning for their identification.

A member of the TNF receptor family, BAFF-R, is fairly divergent from many family members. In particular, BAFF-R contains only one cysteine-rich domain with 4 cysteines, while most TNF receptor family members typically contain 2-4 domains, each with 6 cysteines. This absence of a canonical receptor cysteine-rich domain prevented identification of BAFF-R by sequence-based searches. It was also not clear exactly how BAFF-R achieves high-affinity binding to BAFF, and exactly what sequences are involved.

Not only is BAFF-R distinct from the canonical TNF receptor family members, human BAFF-R (hBAFF-R) is only 60% homologous with murine BAFF-R (mBAFF-R). This difference is reflected in the differential aggregation of hBAFF-R (90% aggregated) and mBAFF-R (10% aggregated) when the extracellular domain is expressed in eukaryotic cells. However, two point mutations in hBAFF-R (V21N and L-28P in SEQ ID NO:1) reduce its aggregation to less than 10%. This mutated form of hBAFF-R is referred to as vBAFF-R.

TNF family members are known to possess both N-linked and O-linked glycosylation sites. N-linked glycosylation occurs on asparagine residues within distinct consensus sequences. O-linked glycosylation occurs on serine and threonine residues, but a lack of sequence motifs and inconsistent addition of sugars within a population of proteins prevents the prediction of the presence of O-linked glycans on a protein. Additionally, O-linked glycosylation sites are often clustered in short serine/threonine-rich sequences, making it difficult to determine the exact number and location of the glycans. Even when a pattern of glycosylation can be determined for a specific protein, O-linked glycosylation is tissue dependent, so the pattern varies with the cell type in which the protein is being expressed.

The ability to analyze any given feature of a batch of protein product may be important for producing polypeptides for pharmaceutical use. The unpredictability and inconsistency of O-linked glycosylation leads to difficulties in manufacturing. For example, a large number of O-linked glycans makes it unfeasible to characterize batches of protein pharmaceuticals by mass spectrometry.

Possible solutions to this problem include the production of proteins in prokaryotic cells, which do not contain glycosylation machinery, and the production of proteins by chemical synthesis. However, glycosylated proteins may have advantages over non-glycosylated proteins. For example, O-linked glycosylation aids in folding and maintaining tertiary structure, causes increased stability and protease resistance, and modulates interactions with other proteins. O-linked glycosylation may also influence a protein's biological activity. It is known that the activity of many cell signaling molecules, including TNFα, is modulated by the glycosylation of cell surface receptors (Van den Steen et al. (1998) *Crit. Rev. Biochem. Mol. Biol.* 33(3): 151-208). Additionally, the production of proteins by chemical synthesis for pharmaceutical use can be prohibitively expensive.

Accordingly, a need exists to provide a BAFF-R protein for therapeutic use with a glycosylation pattern that can be characterized unambiguously, and that avoids aggregation in eukaryotic cells while maintaining specificity and affinity for BAFF.

SUMMARY OF THE INVENTION

The present invention is based, in part, on the discovery and characterization of the glycosylation pattern of human BAFF-R and variants thereof. The invention is further based in part on the discovery and demonstration that the extracellular domain (ECD) of BAFF-R glycoprotein can be truncated without a substantial loss in ligand binding despite the altered glycosylation pattern. The present disclosure provides a non-naturally occurring BAFF-R glycoprotein having a deletion in the ECD that results in an altered O-linked glycosylation pattern. Such truncated forms of BAFF-R are referred to hereinafter as "ΔBAFF-R," or "ΔBAFF-R polypeptides." Corresponding nucleic acids encoding ΔBAFF-R polypeptides are referred to as "ΔBAFF-R nucleic acids."

The present disclosure provides soluble forms of recombinantly expressed ΔBAFF-R that possess at least one or more of the following: an altered glycosylation pattern, an ability to bind to BAFF with an apparent dissociation constant equal to or less than $10^{-9}$ M, and/or a reduced propensity for aggregation. Among other advantages, these truncated forms of BAFF-R possess a glycosylation pattern that allows more efficient analysis of the protein during large-scale production.

In one aspect, the present disclosure provides a truncated form of BAFF-R, having two O-linked glycosylation sites. In certain embodiments, the truncated BAFF-R is glycosylated at T18 of SEQ ID NO:1. In other embodiments, the truncated BAFF-R is glycosylated at T41 of SEQ ID NO:1. In yet other embodiments, ΔBAFF-R is glycosylated at both T18 and T41 of SEQ ID NO:1. Such a glycosylation pattern can be analyzed more efficiently during large-scale production than the full-length ECD of BAFF-R.

In certain embodiments, ΔBAFF-R is human (hBAFF-R). In some embodiments, ΔBAFF-R contains point mutations that reduce the propensity of hBAFF-R to aggregate during recombinant expression, e.g., V21N and L28P of SEQ ID NO:1. The mutated hBAFF-R is referred to as "vBAFF-R."

In particular embodiments, ΔBAFF-R comprises amino acids 13 to 43 of SEQ ID NO:1. In some embodiments, ΔBAFF-R comprises longer amino acid sequences, with the N-terminal amino acid being amino acid 1, 2, 3, 4, 5, 6, 7, 8, 9, 10, 11, 12, 13, 14, 15, 16, 17, 18, or 19 of SEQ ID NO:1 and the C-terminal amino acid being 43, 44, 45, 46, 47, 48, or 49 of SEQ ID NO: 1. In illustrative embodiments, ΔBAFF-R comprises amino acids 1 to 49 of SEQ ID NO:1.

In additional embodiments, the first amino acid sequence may comprise full length BAFF-R comprising mutations at S50, S51, T56, or S63 of SEQ ID NO:1 that remove the ability of the BAFF-R molecule to be glycosylated at these sites. In some embodiments, S50, S51, and T56 of SEQ ID NO:1 are mutated to remove the glycosylation sites. In other embodiments, S50, S51, T56, and S63 are mutated to remove the glycosylation sites.

In certain embodiments, ΔBAFF-R is a part of a BAFF-R fusion polypeptide that comprises (a) a first amino acid sequence encoding ΔBAFF-R polypeptide and (b) a second amino acid sequence derived from the constant region of an immunoglobulin, and optionally, a linker between these sequences.

In certain embodiments of the fusion polypeptide, the first amino acid sequence is substantially identical to amino acids 13 to 43 or amino acids 14 to 43 of SEQ ID NO:1. In other embodiments, ΔBAFF-R comprises longer amino acid sequences, with the N-terminal amino acid being amino acid 1, 2, 3, 4, 5, 6, 7, 8, 9, 10, 11, 12, 13, 14, 15, 16, 17, 18, or 19 of SEQ ID NO:1 and the C-terminal amino acid being 43, 44, 45, 46, 47, 48, or 49 of SEQ ID NO:1. In illustrative embodiments, ΔBAFF-R comprises amino acids 1 to 49 of SEQ ID NO:1, amino acids 8 to 49 of SEQ ID NO:1, amino acids 13 to 49 of SEQ ID NO:1 or amino acids 14 to 49 of SEQ ID NO:1. In all embodiments, the first amino acid sequence does not include amino acids 50 to 56 of SEQ ID NO:1. In some embodiments, the first amino acid sequence does not include amino acids 50 to 63 of SEQ ID NO:1.

The second amino acid sequence may be derived from the constant region of an immunoglobulin, such as the Fc portion. In certain embodiments, the second amino acid sequence is derived from the Fc portion of an IgG. In related embodiments, the Fc portion is derived from $IgG_1$, $IgG_4$, or another IgG isotype. In particular embodiments, the second amino acid sequence is amino acids 3 to 227 of SEQ ID NO:4 (human $IgG_1$).

In certain embodiments, the second amino acid sequence is joined to the C-terminus or the N-terminus of the first amino acid sequence by a linker. The exact length and sequence of the linker and its orientation relative to the linked sequences may vary. The linker may be proteinaceous or non-proteinaceous. In the case of a proteinaceous linker, it does not include amino acids 50 to 56 of SEQ ID NO:1.

In particular embodiments, ΔBAFF-R-Fc fusion polypeptide (ΔBAFF-R:Fc) comprises at least amino acids 1 to 49, 8 to 49, 14 to 49, 13 to 43, or 14 to 43 of SEQ ID NO:1 fused directly to amino acids 3-227 of SEQ ID NO:4. In further embodiments, ΔBAFF-R:Fc comprises amino acids 1 to 49, 8 to 49, 14 to 49, 13 to 43, or 14 to 43 of SEQ ID NO:1 joined indirectly (i.e., through a linker) to amino acids 3 to 227 of SEQ ID NO:4. In some embodiments, ΔBAFF-R:Fc comprises longer BAFF-R sequences, with the N-terminal amino acid being amino acid 1, 2, 3, 4, 5, 6, 7, 8, 9, 10, 11, 12, 13, 14, 15, 16, 17, 18, or 19 of SEQ ID NO:1 and the C-terminal amino acid being amino acid 43, 44, 45, 46, 47, 48, or 49 of SEQ ID NO:1 fused directly to amino acids 3 to 227 of SEQ ID NO:4 or joined by a linker.

The disclosure provides ΔBAFF-R nucleic acids encoding ΔBAFF-R polypeptides. In some embodiments, the nucleic acid comprises sequences encoding at least amino acids 13 to 43 of SEQ ID NO:1 or at least amino acids 14 to 43 of SEQ ID NO:1. The nucleic acid can encode longer fragments of ΔBAFF-R with the N-terminus at amino acid 1, 2, 3, 4, 5, 6, 7, 8, 9, 10, 11, 12, 13, 14, 15, 16, 17, 18, or 19 of SEQ ID NO:1 and the C-terminus at amino acid 43, 44, 45, 46, 47, 48, or 49 of SEQ ID NO:1. In other embodiments, the nucleic acid comprises nucleotides 1 to 216 of SEQ ID NO:2 or nucleotides 1 to 216 of SEQ ID NO:3.

In some embodiments, the invention provides a DNA construct encoding ΔBAFF-R joined to a constant region of an immunoglobulin, either directly or through a linker. In particular embodiments, the DNA construct encodes ΔBAFF-R having an N-terminus at amino acid 1, 2, 3, 4, 5, 6, 7, 8, 9, 10, 11, 12, 13, 14, 15, 16, 17, 18, or 19 of SEQ ID NO:1 and a C-terminus at amino acid 43, 44, 45, 46, 47, 48, or 49 of SEQ ID NO:1, joined to amino acids 3 to 227 of SEQ ID NO:4. In other particular embodiments, the DNA construct comprises nucleotides 1 to 216 of SEQ ID NO:2 or SEQ ID NO:3 joined to nucleotides 7 to 681 of SEQ ID NO:5.

The disclosure also provides methods and pharmaceutical compositions for treating B-cell- and T-cell-mediated conditions. The methods include administering, to a subject in which such treatment is desired, a nucleic acid encoding ΔBAFF-R or a ΔBAFF-R polypeptide in an amount sufficient to treat, prevent, or delay a BAFF-related condition in the subject. The disorders that can be treated using the compositions and methods of the present invention include but are not limited to disorders described in WO 02/24909, herein incorporated by reference. These disorders include, but are not limited to, immunologic disorders, autoimmune diseases, cancers, renal diseases, virus-associated diseases, hypertensive diseases, conditions requiring immunosuppression, inflammatory diseases, and non-malignant proliferative disorders.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIGS. 6A-6B show the location of predicted N-linked glycosylation site on murine BAFF-R:Fc (SEQ ID NO:6) and O-linked glycosylation sites on human vBAFF-R(R3-A72) (SEQ ID NO:1).

DESCRIPTION OF THE EMBODIMENTS

Figure 1:
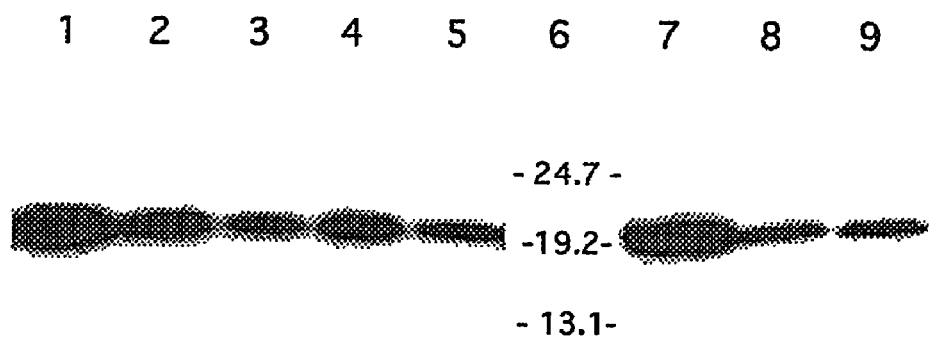
FIG. 1 shows results of co-immunoprecipitation of BAFF with various ΔBAFF-R:Fc. Lane 1 represents amino acids A14 to A72 of SEQ ID NO:1; lane 2 represents amino acids R3 to S50 of SEQ ID NO:1; lane 3 represents amino acids R3 to Q59 of SEQ ID NO:1; lane 4 represents amino acids R3 to G67 of SEQ ID NO:1; lane 5 represents amino acids R3 to A72 of SEQ ID NO:1; lane 6 represents molecular weight standards; lane 7 represents amino acids R3 to A72 of SEQ ID NO:1; lanes 8 and 9 represent amino acids R3 to R43 of SEQ ID NO:1; lane 10 represents amino acids R3 to T41 of SEQ ID NO:1; and lane 11 represents amino acids R3 to C36 of SEQ ID NO:1.

In order for the present invention to be more readily understood, certain terms are defined herein. Additional definitions are set forth throughout the detailed description.

The term "altered glycosylation pattern" refers to a glycosylation pattern on non-naturally occurring BAFF-R having a C-terminally truncated extracellular domain as compared to BAFF-R having the full length extracellular domain, which may or may not differ from wild type sequence. For human BAFF-R, the C-terminal truncation of the extracellular domain is such that it results in removal of at least one O-linked glycosylation site.

The term "BAFF" refers to B-cell-activating factor of the TNF family, characterized by expression by monocytes, macrophages, peripheral blood lymphocytes, and dendritic cells, and its role as a B cell survival factor. A summary of BAFF's characteristics is provided in Mackay et al. (2002) *Nature Reviews: Immunology* 2: 465-475.

As used herein, the term "BAFF-R," unless otherwise stated, refers to mutant or wildtype human BAFF receptor and variants thereof, including the splice variant containing an additional alanine at amino acid 50, as set forth in SEQ ID NO:7, a TNF family receptor protein that binds BAFF, but not the other ligands recognized by BCMA and TACI, as defined in WO 02/24909. The term "ΔBAFF-R" refers to any form of BAFF-R lacking amino acids at the N- or C-terminal, but maintaining the ability to bind to BAFF. The term "hBAFF-R" refers to human BAFF-R protein, or a naturally occurring variant thereof. The term "vBAFF-R" refers to a mutated form of human BAFF-R having mutations at least at amino acids 21 and 28 of SEQ ID NO:1, e.g., V21N and L28P.

The term "BAFF-R:Fc" refers to a fusion protein comprising BAFF-R and immunoglobulin constant region (Fc) sequences. The term "ΔBAFF-R:Fc" refers to any fusion protein comprising (1) at least amino acids 13-43 of SEQ ID NO:1 or a variant thereof, however, not including amino acids 50-56 of SEQ ID NO:1, and (2) an amino acid sequence derived from the constant region of an immunoglobulin, e.g., Fc. Similarly, the term "mBAFF-R:Fc" refers to a fusion protein comprising murine BAFF-R and Fc sequences.

The term "correspond" and its cognates, when used in reference to an amino acid residue or its position, refer to an amino acid position in a first amino acid sequence relative to an amino acid position in a second amino acid sequence when the first and second sequences are optimally aligned. Sequences are considered to be optimally aligned when the maximal possible number of amino acids in both sequences match.

The term "biological activity" refers to a function or set of functions (or the effect to which the function is attributed to) performed by a molecule in a biological system, which may be in vivo or in vitro. Biological activity may be assessed by, for example, the effect on lymphocyte proliferation, survival, and function (e.g., cytokine secretion), cluster of differentiation marker expression, gene expression at the transcriptional, translational, or post-translational levels, or the effect on autoantibody production, etc.

The term "extracellular domain (ECD) of BAFF-R" refers to the portion of the protein present on the exterior of a cell expressing the protein, specifically amino acids 1 to 72 of SEQ ID NO:1. The term "stalk domain" refers to the portion of a TNF receptor family member protein between the cysteine-rich domain and the transmembrane domain.

The term "immunologic disorder" refers to disorders and conditions in which an immune response is aberrant. The aberrant response can be due to (a) abnormal proliferation, maturation, survival, differentiation, or function of immune cells such as, for example, T or B cells. Such disorders include but are not limited to rheumatoid arthritis (RA), juvenile chronic arthritis, asthma, psoriasis, demyelinating disorders, multiple sclerosis (MS), inflammatory bowel disease (IBD), inflammatory and fibrotic lung disease, Crohn's disease, systemic lupus erythematosis (SLE), type I diabetes, transplant rejection, graft-versus-host disease (GVHD), hyperproliferative immune disorders, autoimmune diseases, B cell cancers, immunomodulation, antibody-mediated pathologies (e.g., ITP, myasthenia gravis, and the like), renal diseases, indirect T cell immune response, graft rejection, and graft versus host disease, and immunosuppressive disorders.

The term "isolated" refers to a molecule that is substantially free of its natural environment. For instance, an isolated protein is substantially free of cellular material or other proteins from the cell or tissue source from which it is derived. The term "isolated" also refers to preparations where the isolated protein is sufficiently pure to be administered as a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

The term "modulating" and its cognates refer to a reduction or an increase in biological activity of BAFF-R or BAFF, e.g., the activity associated with the effect exerted by naturally expressed BAFF-R or BAFF on a lymphocyte expressing a BAFF receptor. A reduction or an increase in biological activity is preferably at least 10%, 20%, 30%, 40%, 50%, 60%, 70%, 80%, 90%, or more.

The terms "therapeutic compound" and "therapeutic," as used herein, refer to any compound capable of ameliorating clinical manifestations of a disorder, or producing a desired biological outcome.

The terms "polynucleotide," "oligonucleotide," and "nucleic acid" refer to deoxyribonucleic acid (DNA) and, where appropriate, to ribonucleic acid (RNA), or peptide nucleic acid (PNA). The term should also be understood to include nucleotide analogs, and single or double stranded polynucleotides. Examples of polynucleotides include but are not limited to plasmid DNA or fragments thereof, viral DNA or RNA, antisense RNA, siRNA, etc. The term "plasmid DNA" refers to double stranded DNA that is circular.

The present invention is based, in part, on the discovery and characterization of the glycosylation pattern of human BAFF-R and variants thereof. In particular, the full-length human BAFF-R comprises multiple O-linked glycosylation sites, while the murine version of the protein contains one N-linked glycosylation site and no O-linked glycosylation sites. There are five potential glycosylation sites in the C-terminus of human BAFF-R: T41, S50, S51, T56, and S63 of SEQ ID NO:1. A proteolytic fragment containing all five sites was consistently >80% glycosylated (see Table 2).

The present disclosure provides a non-naturally occurring BAFF-R glycoprotein having a deletion in the ECD that results in altered O-linked glycosylation pattern. Deletion analysis of the stalk region of hBAFF-R(R3-A72):Fc indicates that the deletion of residues 44-72 does not destroy the ability of the resultant fusion protein to interact with BAFF. The fusion protein vBAFF-R(R3-A49):Fc illustrated in the Examples is generated by deletion of amino acid residues 50-72 in the stalk region of vBAFF-R(R3-A72):Fc (described in WO 02/24909).

Determining the exact composition of a protein is an essential step in producing a pharmaceutically acceptable protein-based therapeutic. Variations in the glycosylation of a polypeptide may lead to changes in important characteristics such as binding affinity and solubility. When manufacturing a protein therapeutic, each batch must be analyzed for a variety of important characteristics, including sugar content. The glycosylation pattern of human BAFF-R can be difficult to analyze and control during product manufacturing. Furthermore, given a potential batch-to-batch variability, the analysis of the glycosylation pattern may be necessary for identifying the source of variability. Therefore, among other advantages, the presently disclosed truncated forms of BAFF-R allow for more efficient analysis during large scale production.

The C-terminal truncation of BAFF-R at amino acid 43 produces a polypeptide with just two C-linked glycosylation sites while retaining the BAFF-binding ability of full-length BAFF-R. This ΔBAFF-R is typically glycosylated at only two sites (T18 and T41 of SEQ ID NO:1) when expressed in eukaryotic cells. Thus, the invention provides a biologically active ΔBAFF-R with an altered glycosylation pattern as compared to full-length protein.

The invention is further based, in part, on the discovery that binding of BAFF-R to BAFF still occurs when the N-terminal and/or the C-terminal region of the extracellular domain of BAFF-R is deleted. Binding was not reduced after the deletion of amino acids 50-72 of SEQ ID NO:1, and was only partially reduced after the deletion of amino acids 43-72 of SEQ ID NO:1.

Optimally, ΔBAFF-R:Fc binds to BAFF with an apparent affinity ($k_D^{APP}$) of less than 1 nM. ΔBAFF-R(R3-49):Fc binds to BAFF-expressing cells as well as the full-length form, and prevents the binding of BAFF to cells expressing endogenous BAFF-R at concentrations similar to BAFF-R:Fc. These findings indicate that truncated and full-length BAFF-R:Fc polypeptides possess similar binding affinities for BAFF, and that these affinities are in the sub-nanomolar range. These results are reported as an apparent affinity, which includes an avidity component.

In one aspect, the present disclosure provides a truncated form of BAFF-R, having two O-linked glycosylation sites. In certain embodiments, the truncated BAFF-R is glycosylated at T18 of SEQ ID NO:1. In other embodiments, the truncated BAFF-R is glycosylated at T41 of SEQ ID NO:1. In yet other embodiments, ΔBAFF-R is glycosylated at both T18 and T41 of SEQ ID NO:1. In additional embodiments, ΔBAFF-R may be glycosylated at S8 of SEQ ID NO:1. Such a glycosylation pattern can be analyzed more efficiently during large-scale production than that of the full-length ECD of BAFF-R.

In certain embodiments, ΔBAFF-R is human (hBAFF-R). In some embodiments, ΔBAFF-R contains point mutations that reduce the propensity of hBAFF-R to aggregate during recombinant expression, e.g., V21N and L28P of SEQ ID NO:1. The mutated hBAFF-R is referred to as vBAFF-R.

In particular embodiments, ΔBAFF-R comprises amino acids 13 to 43 of SEQ ID NO:1. In some embodiments, ΔBAFF-R comprises longer amino acid sequences, with the N-terminal amino acid being amino acid 1, 2, 3, 4, 5, 6, 7, 8, 9, 10, 11, 12, 13, 14, 15, 16, 17, 18, or 19 of SEQ ID NO:1 and the C-terminal amino acid being 43, 44, 45, 46, 47, 48, or 49 of SEQ ID NO:1. In illustrative embodiments, ΔBAFF-R comprises amino acids 1 to 49 of SEQ ID NO:1.

In certain embodiments, ΔBAFF-R is a part of a BAFF-R fusion polypeptide that comprises (a) a first amino acid sequence encoding ΔBAFF-R polypeptide and (b) a second amino acid sequence derived from the constant region of an immunoglobulin, and optionally, a linker between these sequences.

In certain embodiments of the fusion polypeptide, the first amino acid sequence is substantially identical to amino acids 13 to 43 of SEQ ID NO:1 or to amino acids 14 to 43 of SEQ ID NO:1. In other embodiments, ΔBAFF-R comprises longer amino acid sequences, with the N-terminal amino acid being amino acid 1, 2, 3, 4, 5, 6, 7, 8, 9, 10, 11, 12, 13, 14, 15, 16, 17, 18, or 19 of SEQ ID NO:1 and the C-terminal amino acid being 43, 44, 45, 46, 47, 48, or 49 of SEQ ID NO:1. In illustrative embodiments, ΔBAFF-R comprises amino acids 1 to 49 of SEQ ID NO:1, amino acids 8 to 49 of SEQ ID NO:1, amino acids 13 to 49 of SEQ ID NO:1, or amino acids 14 to 49 of SEQ ID NO:1. In all embodiments, the first amino acid sequence does not include amino acids 50 to 56 of SEQ ID NO:1. In some embodiments, the first amino acid sequence does not include amino acids 50 to 63 of SEQ ID NO:1.

The second amino acid sequence may be derived from the constant region of an immunoglobulin, such as the Fc portion. In certain embodiments, the second amino acid sequence is derived from the Fc portion of an IgG. In related embodiments, the Fc portion is derived from $IgG_1$, $IgG_4$, or another IgG isotype. In particular embodiments, the second amino add sequence is amino acids 3 to 227 of SEQ ID NO:4 (human $IgG_1$).

In certain embodiments, the second amino acid sequence is joined to the C-terminus or the N-terminus of the first amino acid sequence by a linker. The exact length and sequence of the linker and its orientation relative to the linked sequences may vary. The linker may be proteinaceous or non-proteinaceous. In the case of a proteinaceous linker, it does not include amino acids 50 to 56 of SEQ ID NO:1.

In particular embodiments, ΔBAFF-R-Fc fusion polypeptide (ΔBAFF-R:Fc) comprises at least amino acids 1 to 49, 8 to 49, 14 to 49, 13 to 43, or 14 to 43 of SEQ ID NO:1 fused directly to amino acids 3-227 of SEQ ID NO:4. In further embodiments, ΔBAFF-R:Fc comprises amino acids 1 to 49, 8 to 49, 14 to 49, 13 to 43, or 14 to 43 of SEQ ID NO:1 joined indirectly (i.e., through a linker) to amino acids 3 to 227 of SEQ ID NO:4. In some embodiments, ΔBAFF-R:Fc comprises longer BAFF-R sequences, with the N-terminal amino acid being amino acid 1, 2, 3, 4, 5, 6, 7, 8, 9, 10, 11, 12, 13, 14, 15, 16, 17, 18, or 19 of SEQ ID NO:1 and the C-terminal amino acid being amino acid 43, 44, 45, 46, 47, 48, or 49 of SEQ ID NO:1 fused directly to amino acids 3 to 227 of SEQ ID NO:4 or joined by a linker.

The invention also provides full length BAFF-R molecules comprising amino acid mutations at S50, S51, T56, or S63 of SEQ ID NO:1 that remove the ability of the BAFF-R molecule to be glycosylated at these sites. In some embodiments, S50, S51, and T56 of SEQ ID NO:1 are mutated to remove the glycosylation sites. In other embodiments, S50, S51, T56, and S63 are mutated to remove the glycosylation sites.

The disclosure provides BAFF-R nucleic acids encoding ΔBAFF-R polypeptides. In some embodiments, the nucleic acid comprises sequences encoding at least amino acids 13 to 43 of SEQ ID NO:1 or at least amino acids 14 to 43 of SEQ ID NO:1. The nucleic acid can encode longer fragments of ΔBAFF-R with the N-terminus at amino acid 1, 2, 3, 4, 5, 6, 7, 8, 9, 10, 11, 12, 13, 14, 15, 16, 17, 18, or 19 of SEQ ID NO:1 and the C-terminus at amino acid 43, 44, 45, 46, 47, 48, or 49 of SEQ ID NO:1. In other embodiments, the nucleic acid comprises nucleotides 1 to 216 of SEQ ID NO:2 or nucleotides 1 to 216 of SEQ ID NO:3.

In some embodiments, the invention provides a DNA construct encoding ΔBAFF-R joined to a constant region of an immunoglobulin, either directly or through a linker. In particular embodiments, the DNA construct encodes ΔBAFF-R having an N-terminus at amino acid 1, 2, 3, 4, 5, 6, 7, 8, 9, 10, 11, 12, 13, 14, 15, 16, 17, 18, or 19 of SEQ ID NO:1 and a C-terminus at amino acid 43, 44, 45, 46, 47, 48, or 49 of SEQ ID NO:1, joined to amino acids 3 to 227 of SEQ ID NO:4. In other particular embodiments, the DNA construct comprises nucleotides 1 to 216 of SEQ ID NO:2 or SEQ ID NO:3 joined to nucleotides 7 to 681 of SEQ ID NO:5.

A fusion protein construct can be created by ligating sequences encoding two distinct polypeptides in frame such that they are translated in a single open reading frame. In some embodiments, the invention provides a DNA construct comprising ΔBAFF-R fused to the constant region of an antibody, either directly or with linker DNA that does not include sequence encoding amino acids 50 to 56 of SEQ ID NO:1. In specific embodiments, the nucleic acids can encode a ΔBAFF-R:Fc protein having the N-terminus at amino acid 1, 2, 3, 4, 5, 6, 7, 8, 9, 10, 11, 12, 13, 14, 15, 16, 17, 18, or 19 of SEQ ID NO:1 and the C-terminus at amino acid 43, 44, 45, 46, 47, 48, or 49 of SEQ ID NO:1 linked to amino acids 3 to 227 of SEQ ID NO:4. In other specific embodiments the nucleic acids comprise nucleotides 1 to 216 of SEQ ID NO:2 linked to nucleotides 7 to 681 of SEQ ID NO:5.

ΔBAFF-R and its encoding nucleic acid molecules and vectors may be produced using any suitable cloning methods. Systems for cloning and expression of a polypeptide in a variety of different host cells are well known. Suitable host cells include bacteria, mammalian cells, and yeast and baculovirus systems. Mammalian cell lines available in the art for expression of a heterologous polypeptide include Chinese hamster ovary cells, HeLa cells, baby hamster kidney cells, NSO mouse melanoma cells and many others. A common bacterial host is *E. coli*. Bacterial cells, such as *E. coli*, do not add N-linked or O-linked glycosylation to the polypeptide. Yeast and baculovirus do make N-linked or O-linked glycosylation modifications, but the sugar residues may be of different composition in these cells than those utilized by mammalian cells. For other cells suitable for producing ΔBAFF-R, see *Gene Expression Systems*, eds. Fernandez et al. (1999) Academic Press.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmid or viral, e.g., phage, or phagemid, as appropriate. For further details see, e.g., Molecular Cloning: A Laboratory Manual, Sambrook et al. (1989) 2nd ed., Cold Spring Harbor Laboratory Press. Many known techniques and protocols for manipulation of nucleic acid, for example, in preparation of nucleic acid constructs, mutagenesis, sequencing, introduction of DNA into cells and gene expression, and analysis of proteins, are described in detail in *Current Protocols in Molecular Biology*, eds. Ausubel et al. (1992) 2nd ed., John Wiley & Sons.

The ΔBAFF-R polypeptides of the invention and nucleic acids encoding them can be incorporated into pharmaceutical compositions suitable for administration. Such compositions typically comprise the nucleic acid or polypeptide and a pharmaceutically acceptable carrier. As used herein, "pharmaceutically acceptable carrier" is intended to include any solvents, dispersion media, coatings, antibacterial and antifungal agents, isotonic and absorption delaying agents, and others that are compatible with pharmaceutical administration. Suitable carriers are described in detail in WO 02/24909.

A pharmaceutical composition of the invention is formulated to be compatible with its intended route of administration. A therapeutically effective amount of ΔBAFF-R ranges from 0.001 to 30 mg/kg, preferably from 0.01 to 25 mg/kg, from 0.1 to 20 mg/kg, or from 1 to 10 mg/kg body weight. The dosage may be adjusted, as necessary, to suit observed effects of the treatment. ΔBAFF-R may given as a bolus dose. Continuous infusion may also be used after the bolus dose. The appropriate dose and regimen is chosen based on clinical indications by a treating physician. Examples of routes of administration and appropriate compositions for each of these routes are described in detail in WO 02/24909. Additional methods and therapeutic regiments are described in detain in U.S. Application Ser. No. 60/512,880.

The nucleic acids of the invention can be inserted in vectors and used as gene therapy vectors or delivered as naked DNA. Examples of gene therapy vectors and delivery thereof can be found in WO 02/24909.

The present invention provides both prophylactic and therapeutic methods of treating a subject at risk of (or susceptible to) a BAFF-related disorder (a disorder associated with aberrant BAFF or BAFF-R expression or activity such as, for example, in B-cell- and T-cell-mediated conditions).

Diseases and disorders that are characterized by increased levels or biological activity of BAFF may be treated with therapeutics that antagonize BAFF or BAFF-R activity. The methods include administering, to a subject in which such treatment is desired, a nucleic acid encoding ΔBAFF-R or a ΔBAFF-R polypeptide in an amount sufficient to treat, prevent, or delay a BAFF-related condition in the subject. The disorders that can be treated using the compositions and methods of the present invention include but are not limited to disorders described in WO 02/24909.

Administering the ΔBAFF-R composition can occur prior to the manifestation of symptoms characteristic of the BAFF-R activity, such that a disease or disorder is prevented or, alternatively, delayed in its progression.

Another aspect of the invention pertains to methods of modulating BAFF or BAFF-R expression or activity for therapeutic purposes. The modulatory methods of the invention involves contacting a cell with a ΔBAFF-R polypeptide or nucleic acid that modulates one or more of the activities of BAFF activity associated with the cell. In one embodiment, the ΔBAFF-R composition inhibits one or more BAFF activities. The modulation can be performed in vitro (e.g., by culturing a cell with the composition) or, alternatively, in vivo (e.g., by administering the agent to a subject). As such, the present invention provides methods of treating an individual afflicted with a disease or disorder involving BAFF activity by administering a ΔBAFF-R protein or nucleic acid to block BAFF activity.

The disclosure provides methods and pharmaceutical compositions for treating autoimmune diseases, B cell cancers, immunomodulation, inflammatory bowel disease, and any antibody-mediated pathologies (e.g., ITP, myasthenia gravis, and the like), renal diseases, indirect T cell immune response, graft rejection, and graft versus host disease. The compositions of the invention can be targeted to specifically regulate B cell responses during the immune response. Additionally, the compositions of the invention can be used to modulate B cell development, development of other cells, antibody production, and cytokine production. Compositions of the invention can also modulate T and B cell communication by neutralizing the proliferative effects of BAFF.

The ΔBAFF-R nucleic acids and polypeptides can also be useful for the treatment of autoimmune disorders including, but not limited to, lupus and rheumatoid arthritis. By modulating BAFF activity, ΔBAFF-R may prevent or reduce the symptoms of these diseases. The ΔBAFF-R-mediated modulation of the symptoms of these diseases may occur by the reduction of B cell development, development of other cells, antibody production, or cytokine production. The effect of ΔBAFF-R on lupus may be measured by evaluating autoantibody levels, immune complex deposition complications, and symptoms of systemic lupus erythematosis, including kidney failure, proteineuria, splenomegaly, neuralgic symptoms, and death. The effect of ΔBAFF-R on rheumatoid arthritis may be measured by evaluating autoantibody levels, the secretion of arthritogenic immunoglobulins, joint and extremity swelling, or cytokine levels. In addition, ΔBAFF-R may be useful for treating other autoimmune disorders such as myasthenia gravis and juvenile chronic arthritis.

ΔBAFF-R nucleic acids and polypeptides can be useful for neutralizing the effects of BAFF for treating pre-B or B-cell leukemias, such as plasma cell leukemia, chronic or acute lymphocytic leukemia, myelomas (e.g., multiple myeloma, plasma cell myeloma, endothelial myeloma, and giant cell myeloma), and lymphoma (e.g., non-Hodgkin's lymphoma). Additional examples of B cell lymphomas that may be treated with the molecules described herein include Burkit's lymphoma, non-Burkitts lymphoma, follicular lymphoma, acute lymphoblastic leukemia, large cell lymphoma (e.g., immunoblastic lymphoma), marginal zone lymphoma, mantle cell lymphoma, small lymphocytic lymphoma, and other B cell lymphomas.

The invention provides methods employing ΔBAFF-R polypeptides and nucleic acids for selectively blocking or neutralizing the actions of B cells in association with end stage renal diseases, which may or may not be associated with autoimmune diseases. Such methods would be useful for treating immunologic renal diseases, e.g., glomerulonephritis associated with diseases such as membranous nephropathy, IgA nephropathy, or Berger's disease, IgM nephropathy, Goodpasture's disease, post-infectious glomerulonephritis, mesangioproliferative disease, chronic lymphoid leukemia, and minimal-change nephritic syndrome. Such methods would also serve as therapeutic applications for treating secondary glomerulonephritis or vasculitis associated with such diseases as lupus, polyarteritis, Henoch-Schonlein disease, Scleroderma, HIV-related diseases, amyloidosis, or hemolytic uremic syndrome. The methods of the present invention would also be useful as part of a therapeutic application for treating interstitial nephritis or pyelonephritis associated with chronic pyelonephritis, analgesic abuse, nephrocalcinosis, nephropathy caused by other agents, nephrolithiasis, or chronic or acute interstitial nephritis. The methods of the present invention also include the use of ΔBAFF-R nucleic acids or polypeptides in the treatment of hypertensive or large vessel diseases, including renal artery stenosis or occlusion and cholesterol emboli or renal emboli, renal or urological neoplasms, multiple myelomas, lymphomas, light chain neuropathy, or amyloidosis with compositions comprising ΔBAFF-R.

The invention also provides methods for blocking or inhibiting activated B cells using ΔBAFF-R polypeptides for the treatment of asthma and other chronic airway diseases such as bronchitis and emphysema.

Also provided are methods for inhibiting or neutralizing an effector T cell response using ΔBAFF-R polypeptides. These methods can be used to treat conditions requiring immunosuppression, such as graft-versus-host disease and graft rejection. ΔBAFF-R compositions are also useful for treatment of autoimmune diseases like insulin dependent diabetes mellitus and Crohn's disease. Methods of the present invention would have additional therapeutic value for treating chronic inflammatory diseases, in particular, to lessen joint pain (e.g, in trauma or osteoarthritis), swelling, anemia, and other associated symptoms as well as for treating septic shock.

Additionally, the present invention is useful for the treatment of proliferative conditions that are not considered to be tumors, i.e., cellular hyperproliferation (hyperplasia), such as, for example, scleroderma, pannus formation in rheumatoid arthritis, postsurgical scarring and lung, liver and uterine fibrosis.

EXAMPLE 1

This example describes the generation and analysis of various peptide deletions within the receptor domain of wild type hBAFF-R:Fc. These deletion mutants were analyzed for ability to bind hBAFF.

Double stranded oligonucleotide cassettes with cohesive ends that encode various in-frame peptide deletions within the hBAFF-R domain of hBAFF-R:Fc were designed and synthesized. The oligonucleotide cassettes were ligated with hBAFF-R:Fc containing vectors with complementary termini. Cassettes were designed to eliminate residues either N-terminal to the cysteine-rich domain (CRD) or C-terminal to the CRD in the stalk region.

The coding sequences for hBAFF-R:Fc deletions were subcloned into vectors for mammalian cell expression in 293EBNA cells. Expression plasmids were transfected into 293EBNA cells using Lipofectamine™ (Invitrogen). Transfected cell supernatants were harvested at 48 hr post-transfection.

Expression was evaluated by non-reducing SDS-PAGE followed by Western transfer to PVDF membranes. Membranes were blocked for one hour with 5% non-fat dry milk in TBST (10 mM Tris-Cl, 150 mM NaCl, 0.05% Tween 20™), probed with an HRP-conjugated anti-human IgG antibody (Jackson ImmunoResearch), washed three times in TBST, and detected with a chemiluminescent substrate (ECL, Amersham-Pharmacia).

The ability to bind hBAFF was analyzed by co-immunoprecipitation. In these experiments, 100 µl of conditioned media containing hBAFF-R:Fc or a deletion thereof were incubated 3 hrs or overnight at 4° C. in 1 ml DMEM-10% FBS with 100 ng/ml soluble flag-hBAFF. Protein A Sepharose™ beads, 30 µl, were added and incubated continued with agitation for an additional 90 minutes. Beads were centrifuged briefly and washed 3 times with 1 ml cold PBS. Beads were resuspended in reducing Laemmli buffer, boiled, and run on SDS-PAGE. Western blots were performed as described above with 5 µg/ml anti-flag-HRP (Sigma Chemical) used as a probe.

The coding sequences for the various deletions of hBAFF-R:Fc were screened by various restriction digests and verified by DNA sequencing. All of the constructs expressed Fc fusion proteins at moderate levels but aggregation was not alleviated as compared to hBAFF-R(R3-A72):Fc. Co-immunoprecipitation results are shown in FIG. 1 and summarized in Table 1. In FIG. 1, lane 1 represents amino acids A14 to A72 of SEQ ID NO:1; lane 2 represents amino acids R3 to S50 of SEQ ID NO:1; lane 3 represents amino acids R3 to Q59 of SEQ ID NO:1; lane 4 represents amino acids R3 to G67 of SEQ ID NO:1; lane 5 represents amino acids R3 to A72 of SEQ ID NO:1; lane 6 represents amino acids molecular weight standards; lane 7 represents amino acids R3 to A72 of SEQ ID NO:1; lanes 8 and 9 represent amino acids R3 to R43 of SEQ ID NO:1; lane 10 represents amino acids R3 to T41 of SEQ ID NO:1; and lane 11 represents amino acids R3 to C36 of SEQ ID NO:1. The N-terminal deletion hBAFF-R(A14-A72):Fc retains BAFF binding ability while hBAFF-R(C20-A72):Fc does not. This indicates that all or a subset of the five amino acid residues immediately N-terminal to the hBAFF-R CRD are required for BAFF binding of hBAFF-R:Fc. BAFF binding was eliminated in C-terminal deletions hBAFF-R(R3-C36):Fc and hBAFFR(R3-T41):Fc, and profoundly reduced in hBAFF-R(R3-R43):Fc. All other hBAFF-R:Fc constructs tested that encode BAFF-R through S50 or greater in the hBAFF-R stalk domain are able to co-immunoprecipitate hBAFF as effectively as the full stalk version, hBAFF-R(R3-A72):Fc. Since truncation at R43 allows for partial binding activity and truncation at S50 allows for full activity, it is apparent that residues P44-A49 or a subset thereof are required for proper ligand binding to occur.

TABLE 1

| N-terminus of BAFF-R moiety | C-terminus of BAFF-R moiety | Comments | BAFF binding (co-IP) |
|---|---|---|---|
| R3 | A72 | full length R-Fc | +++ |
| R3 | G67 | eliminates short hydrophobic stretch in c-terminal domain | +++ |
| R3 | Q59 | best alignment with hBCMA-Fc hydrophobicity plot | +++ |
| R3 | S50 | intermediate length C-terminal deletion | +++ |
| R3 | R43 | intermediate length C-terminal deletion | + |
| R3 | T41 | intermediate length C-terminal deletion | − |
| R3 | C36 | maximal C-terminal deletion without interrupting cysteine-rich domain | − |
| A14 | A72 | eliminates highly basic stretch in N-terminal domain | +++ |
| C20 | A72 | maximal N-terminal deletion without interrupting cysteine-rich domain | − |
| R3 | G82 | addition of 10 residues of potential stalk domain | +++ |

EXAMPLE 2

This example describes the design, construction and sequence of a version of vBAFF-R(R3-A72):Fc containing a truncated BAFF-R stalk domain. The fusion protein vBAFF-R(R3-A49):Fc was created in order to remove the four potential O-linked glycosylation sites located at residues S50, S51, T56, and S63 of SEQ ID NO:1.

A double stranded oligonucleotide cassette with cohesive ends was used to replace nucleotides encoding BAFF-R amino acid residues C33 to A72 with nucleotides encoding amino acid residues C33 to A49 by ligation into the same sites in the vBAFF-R(R3-A72):Fc coding sequence. The sequences of these oligonucleotides, baf-911 and baf-912, are shown in SEQ ID NO:8 and SEQ ID NO:9. This oligonucleotide replacement results in the elimination of residues S50A72 of vBAFF-R(R3-A72):Fc.

The vBAFF-R(R3-A49):Fc coding sequence was subcloned into vectors for mammalian cell expression, specifically, 293EBNA or CHO cells. Expression plasmids were transfected into 293EBNA cells using Lipofectamine® (Invitrogen). Transfected cell supernatants were harvested at 96 hours post transfection. The fusion protein vBAFF-R(R3-A49):Fc was purified by protein A affinity chromatography and gel filtration size exclusion chromatography.

EXAMPLE 3

This example illustrates the determination of the apparent binding affinity of both full-length vBAFF-R:Fc and truncated vBAFF-R:Fc for BAFF by analysis of their solution phase binding by BIAcore™.

All measurements were made on a BIAcore™ 3000. BCMA-Fc was immobilized to a high density on one quadrant of a CM5 chip, and one quadrant was left underivitized as a background control.

A standard curve for the amount of free BAFF was established by running successive samples containing various concentrations of BAFF over the chip surfaces. The initial rate of binding ($V_1$) was plotted as a function of BAFF concentration. Under the conditions used $V_1$ is proportional to the amount of free BAFF in solution.

Figure 2:
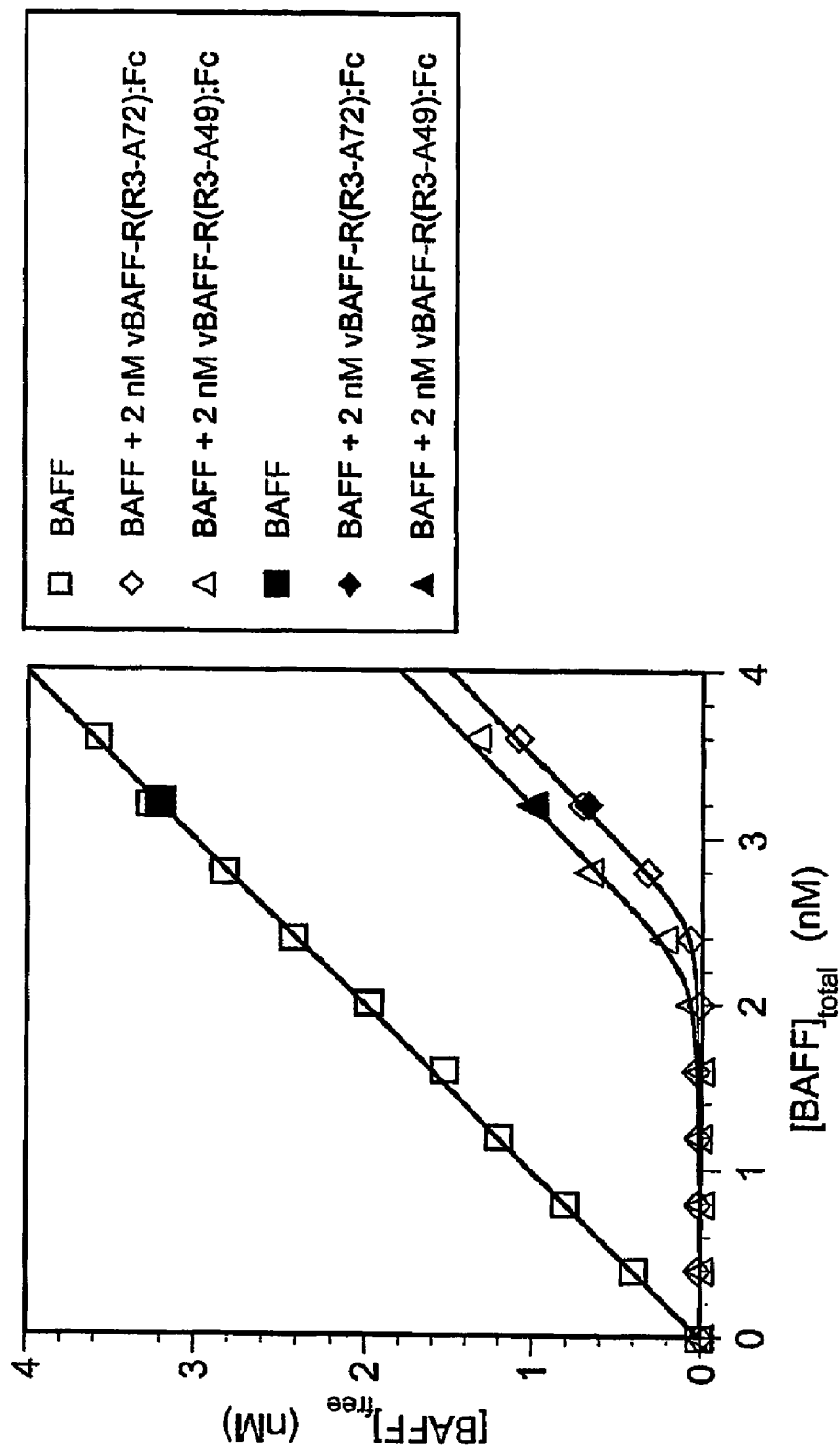
FIG. 2 shows results of a binding assay for determination of $k_D^{APP}$ of vBAFF-R(R3-A49):Fc or vBAFF-R(R3-A72):Fc, and BAFF. The open and closed symbols represent the results from duplicate experiments.

As shown in FIG. 2, the equilibrium binding of BAFF to each form of BAFF-R:Fc, in solution, was determined by pre-mixing various concentrations of BAFF with a fixed amount of either vBAFF-R(R3-A72):Fc or vBAFF-R(R3-A49):Fc, and allowing these solutions to come to equilibrium. These solutions were then run over the BCMA-Fc chip surface and the amount of free BAFF in each solution was determined from $V_1$ by comparison to the standard curve. The affinity and stoichiometry of binding were determined by fitting the data to the appropriate quadratic equation.

Figure 3:
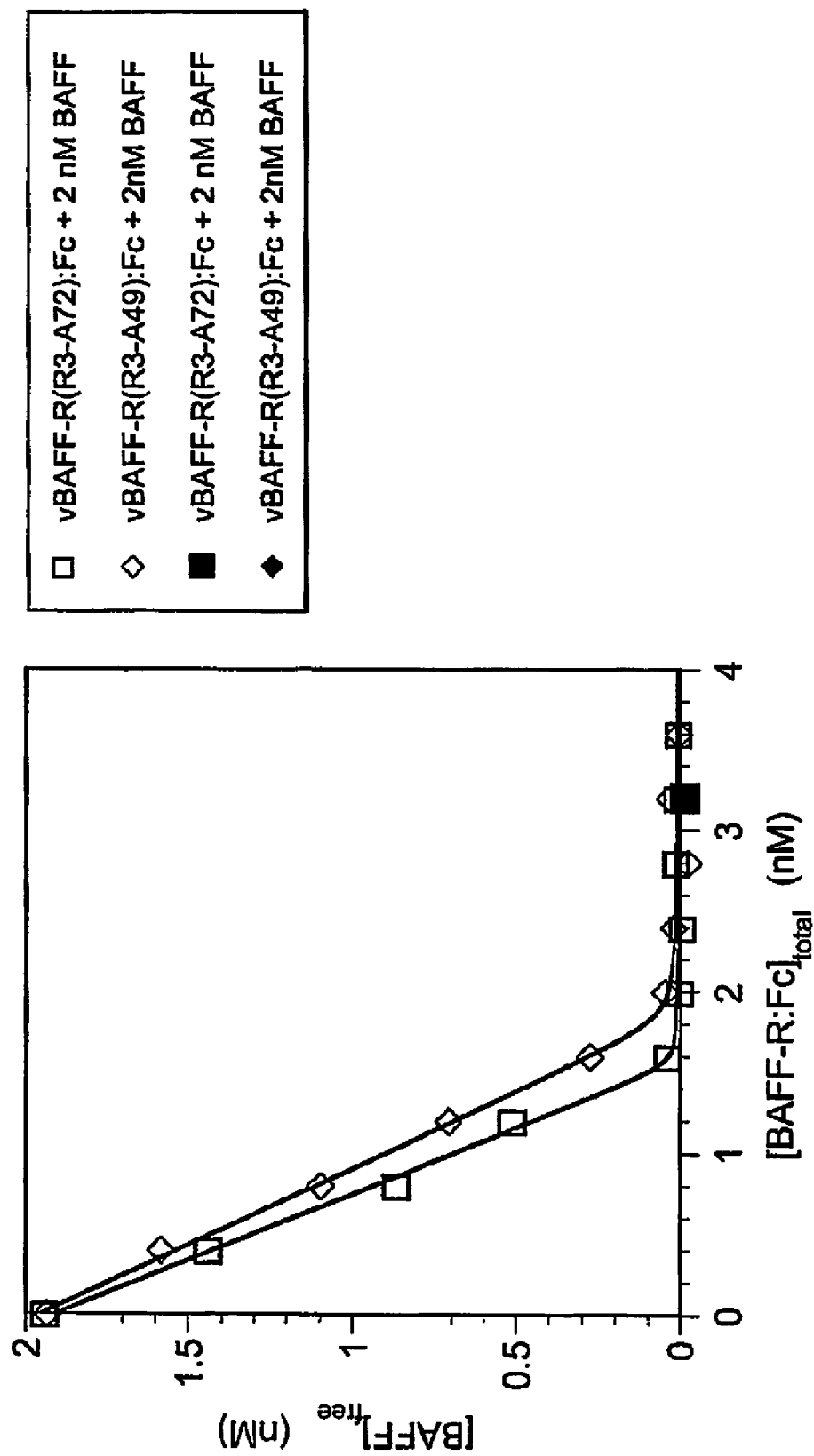
FIG. 3 shows an analysis of the estimated $k_D^{APP}$ of vBAFF-R(R3-A49):Fc or vBAFF-R(R3-A72):Fc, and BAFF. The open and closed symbols represent the results from duplicate experiments.

As shown in FIG. 3, the equilibrium binding of BAFF to vBAFF—R(R3-A72):Fc and vBAFF-R(R3-A49):Fc in solution was determined by pre-mixing various concentrations of each form of variant BAFF-R:Fc with a fixed amount of BAFF and allowing these solutions to come to equilibrium. These VBAFF-R:Fc/BAFF mixtures were then run over the BCMA-Fc chip surface and the amount of free BAFF in each solution was determined from $V_1$. The affinity and stoichiometry of binding were determined by fitting the data to the appropriate quadratic equation.

As displayed in FIGS. 2 and 3, the binding affinities of vBAFF-R(R3-A72):Fc and vBAFF-R(R3-A49):Fc for BAFF are identical by these methods. vBAFF-R(R3-A72):Fc and vBAFF-R(R3-A49):Fc bind to BAFF in solution with an apparent $K_D$<200 pM and a 1:1 (BAFF:BAFF-R:Fc) stoichiometry.

EXAMPLE 4

This example illustrates the ability of vBAFF-R(R3-A49):Fc to bind to a CHO cell line stably expressing human BAFF on its surface (CHO:hBAFF).

Three-fold serial dilutions, ranging from 9 μg/ml to 4 ng/ml, of purified vBAFF-R(R3-A72):Fc or vBAFF-R(R3-A49):Fc were incubated for one hour on ice with CHO:hBAFF cells ($5 \times 10^6$ cells/ml). Cells were washed with FACS buffer and stained with donkey anti-human IgG-PE (Jackson ImmunoReseach) for 30 minutes on ice. Cells were washed in FACS buffer and fixed in 1% paraformaldehyde. Cells were analyzed by FACS for PE fluorescence and the mean fluorescence of the histograms was plotted.

Figure 4:
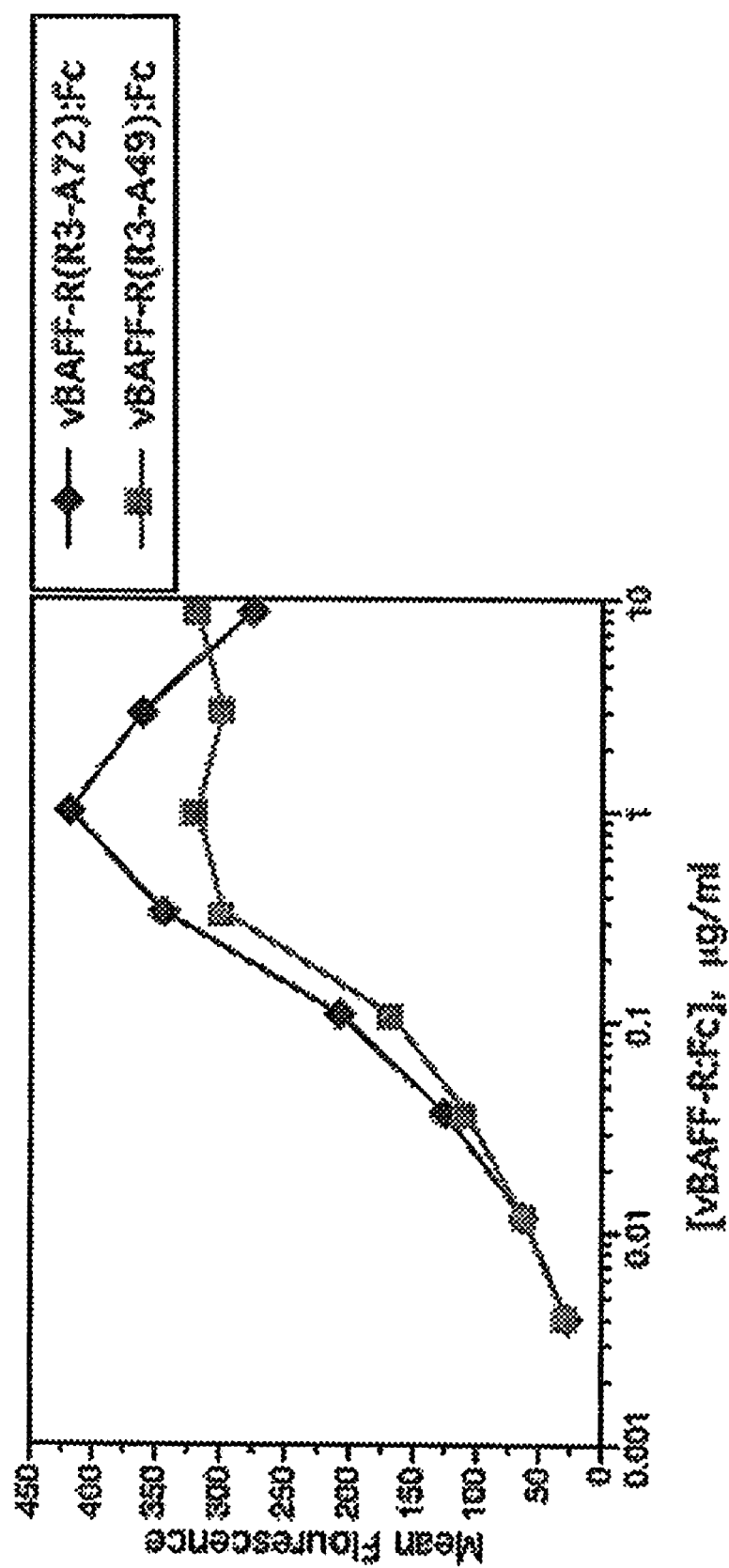
FIG. 4 shows the binding of vBAFF-R(R3-A72):Fc and vBAFF-R(R3-A49):Fc to human BAFF (hBAFF) expressed on the surface of CHO cells.

FIG. 4 shows the binding curves for vBAFF-R(R3-A72):Fc and vBAFF-R(R3-A49):Fc to CHO:hBAFF cells. The two curves nearly overlay one another and show similar values for half-maximum binding to the CHO:hBAFF cells.

EXAMPLE 5

This example illustrates the ability for vBAFF-R(R3-A72):Fc and vBAFF-R(R3-A49):Fc to block the binding of hBAFF to BJAB cells, a human B cell line that expresses hBAFF-R on its surface.

Biotinylated myc-hBAFF was simultaneously added to BJAB cells ($5 \times 10^6$ cells/ml) with either FACS™ buffer or with three-fold serial dilutions of purified vBAFF-R(R3-A72):Fc or vBAFF-R(R3-A49):Fc. The final concentration of biotinylated hBAFF was 200 ng/ml and the concentrations of the vBAFF-R:Fc molecules ranged from 9 μg/ml to 4 ng/ml. The cells were incubated with these solutions on ice for one hour. Cells were washed with FACS™ buffer, stained with SAV-PE on ice for 30 min, washed again and fixed in 1% paraformaldehyde. The cells were analyzed by FACS™ for PE fluorescence and the mean fluorescence of the histograms was plotted.

Figure 5:
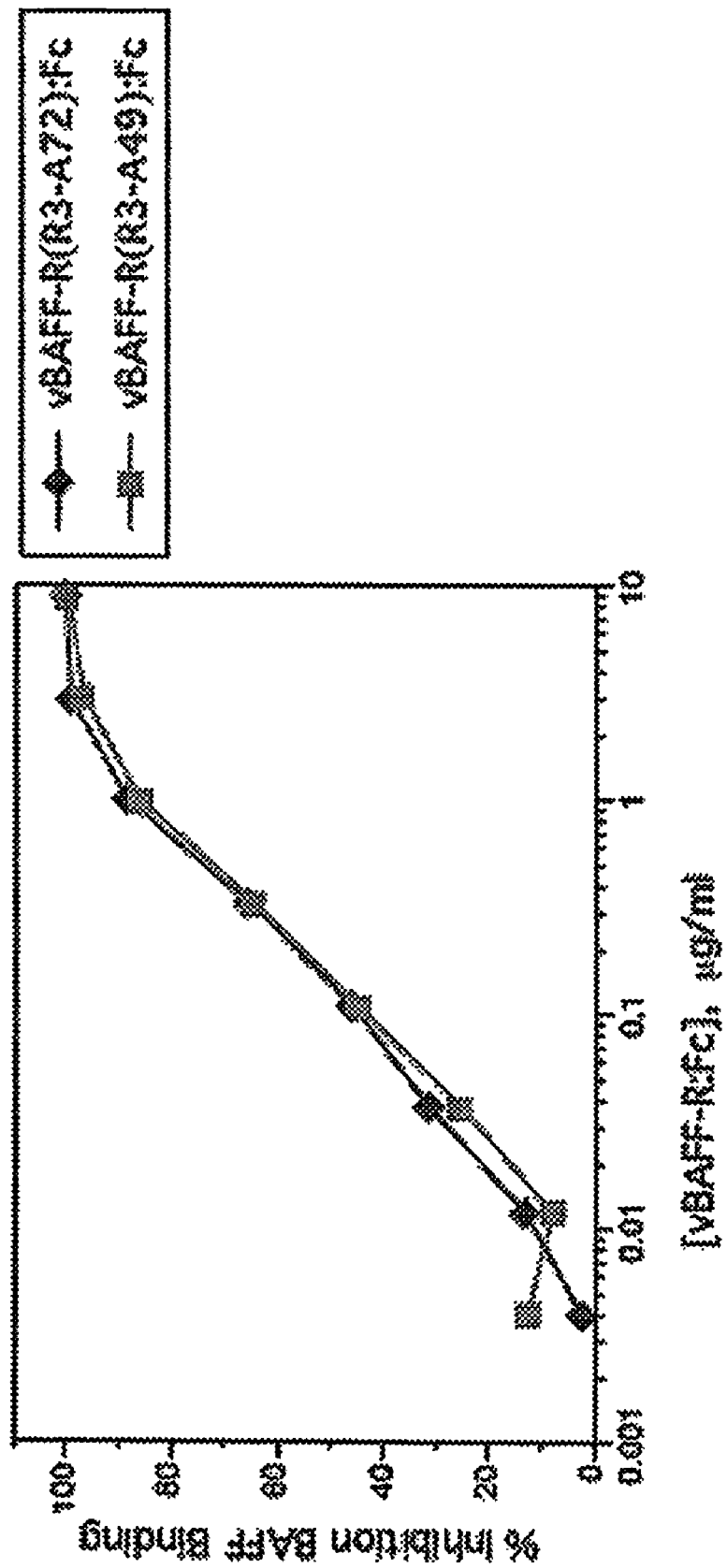
FIG. 5 shows results of binding assays with various concentrations of vBAFF-R(R3-A72):Fc or vBAFF-R(R3-A49):Fc to block the binding of biotinylated hBAFF to BJAB cells.

FIG. 5 shows the curves for the ability of various concentrations of vBAFF-R(R3-A72):Fc or VBAFF-R(R3-A49):Fc to block the binding of biotinylated hBAFF to BJAB cells. The two curves nearly precisely overlay one another. Half-maximal inhibition of hBAFF binding to BJAB cells for vBAFF-R(R3-A72):Fc and vBAFF-R(R3-A49):Fc are similar.

EXAMPLE 6

This example demonstrates the glycosylation patterns of human vBAFF-R(R3-A72):Fc and vBAFF-R(R3-A49):Fc. The predicted N-linked glycosylation site in the mouse BAFF-R molecule and O-linked glycosylation sites in the human BAFF-R molecule are shown in FIGS. 6A and 6B.

vBAFF-R(R3-A72):Fc and vBAFF-R(R3-A49):Fc were expressed and purified from CHO cells by incubation with Protein A Sepharose™, acid elution, and gel filtration chromatography. After treatment with PNGase F to remove N-linked glycans, the proteins were reduced with DTT, and molecular mass was determined using a ZMD mass spectrometer. The molecular masses were generated by deconvolution with the MasEnt 1 program.

Figure 7:
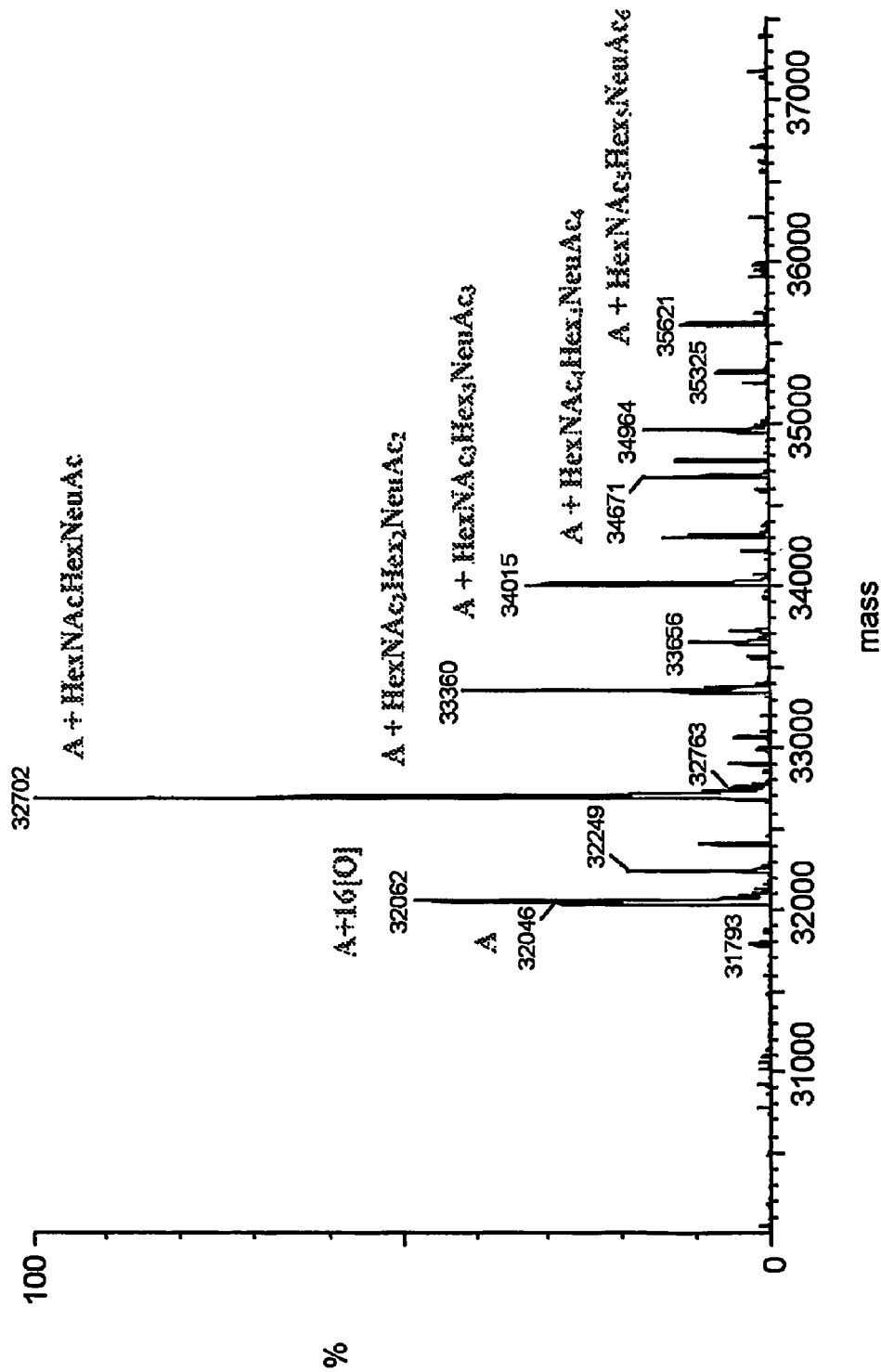
FIG. 7 shows a mass spectrum of vBAFF-R(R3-A72):Fc isolated from a CHO clone, indicating the molecular weights of the O-linked glycosylation forms associated with each peak.
Figure 8A:
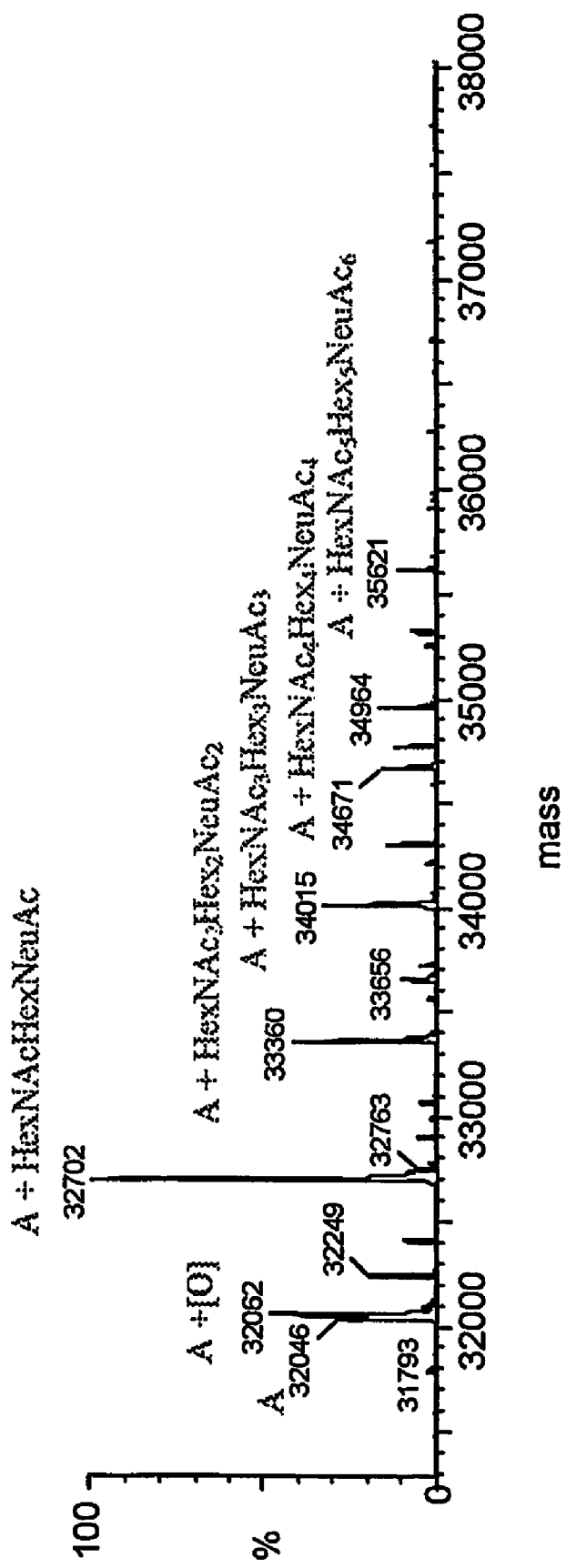
FIGS. 8A-8F show mass spectra of vBAFF-R(R3-A72):Fc's isolated from various CHO clones.
Figure 8B:
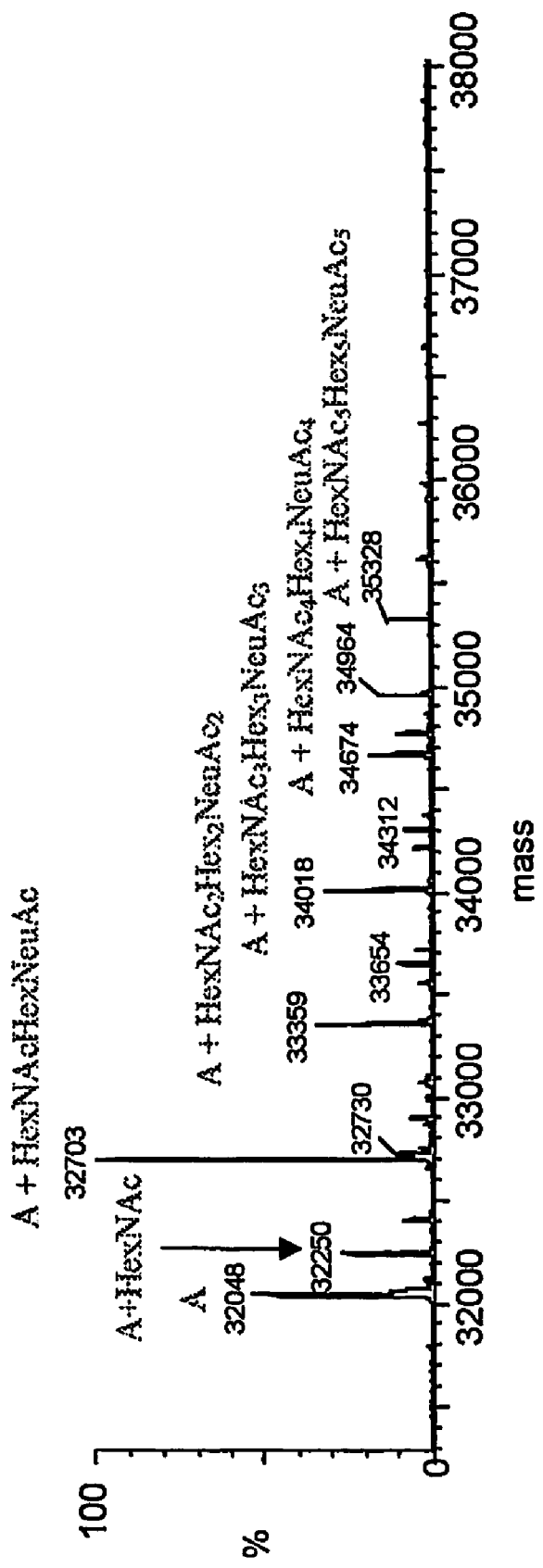
Figure 8C:
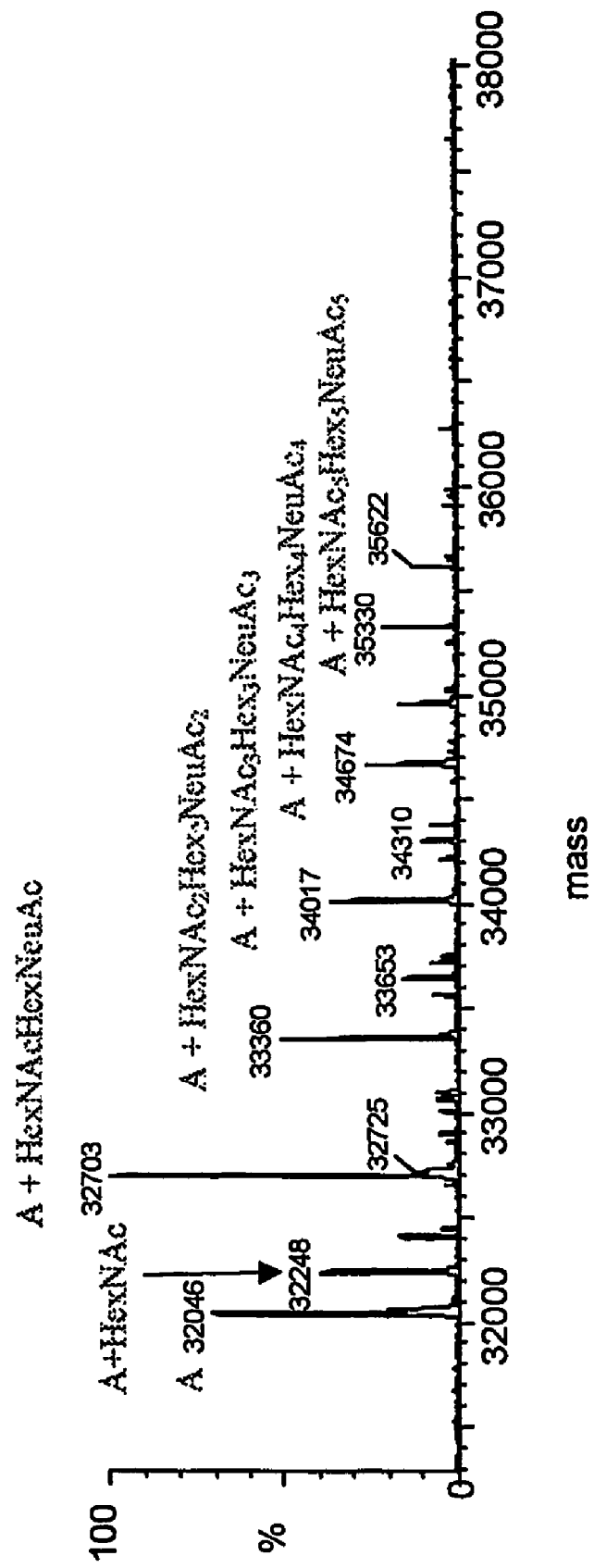
Figure 8D:
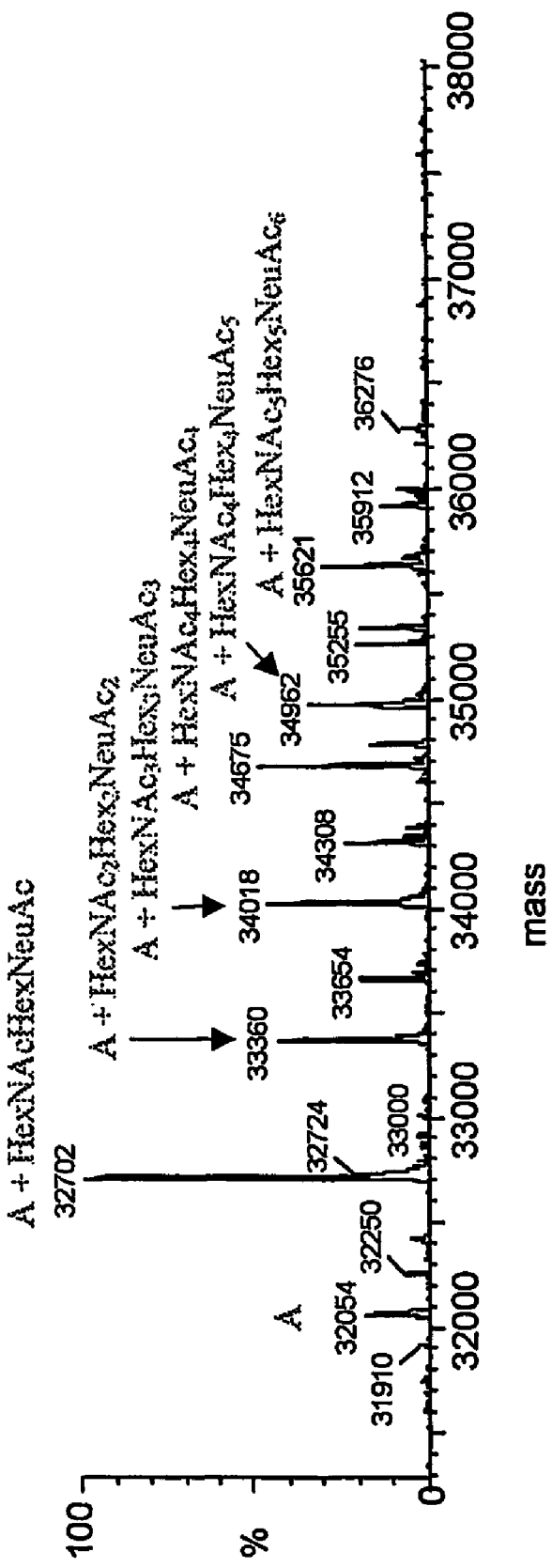
Figure 8E:
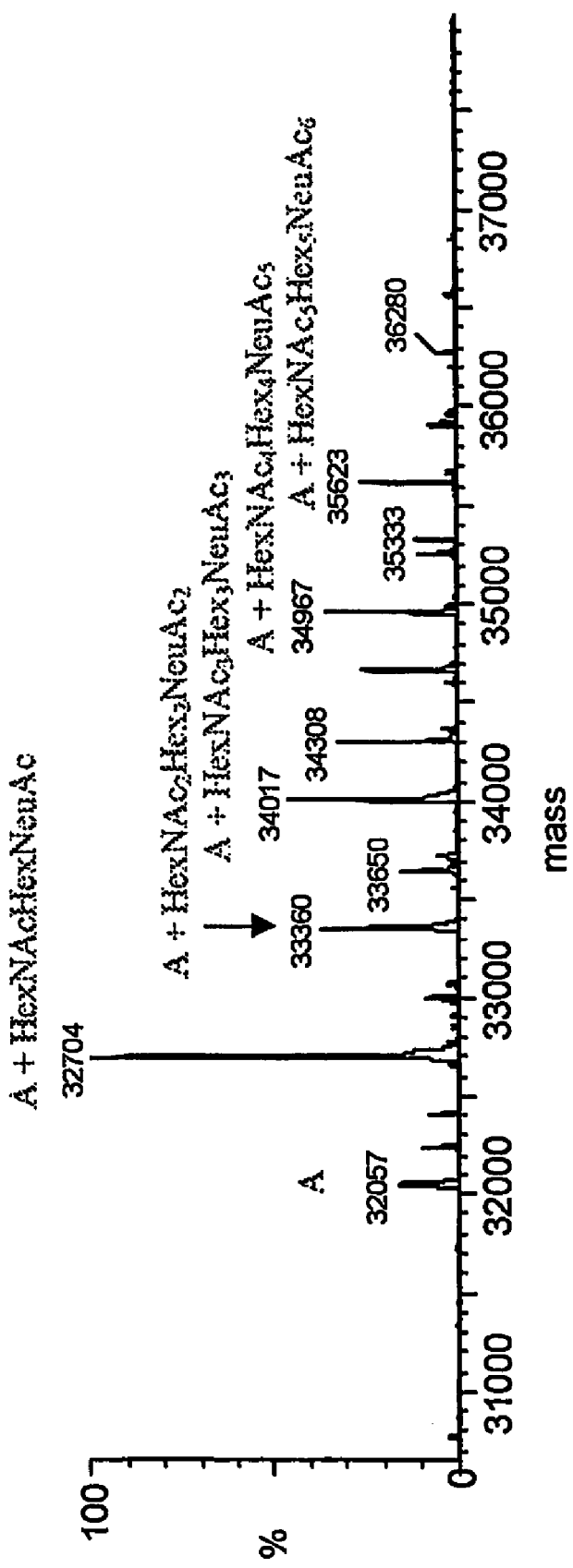
Figure 8F:
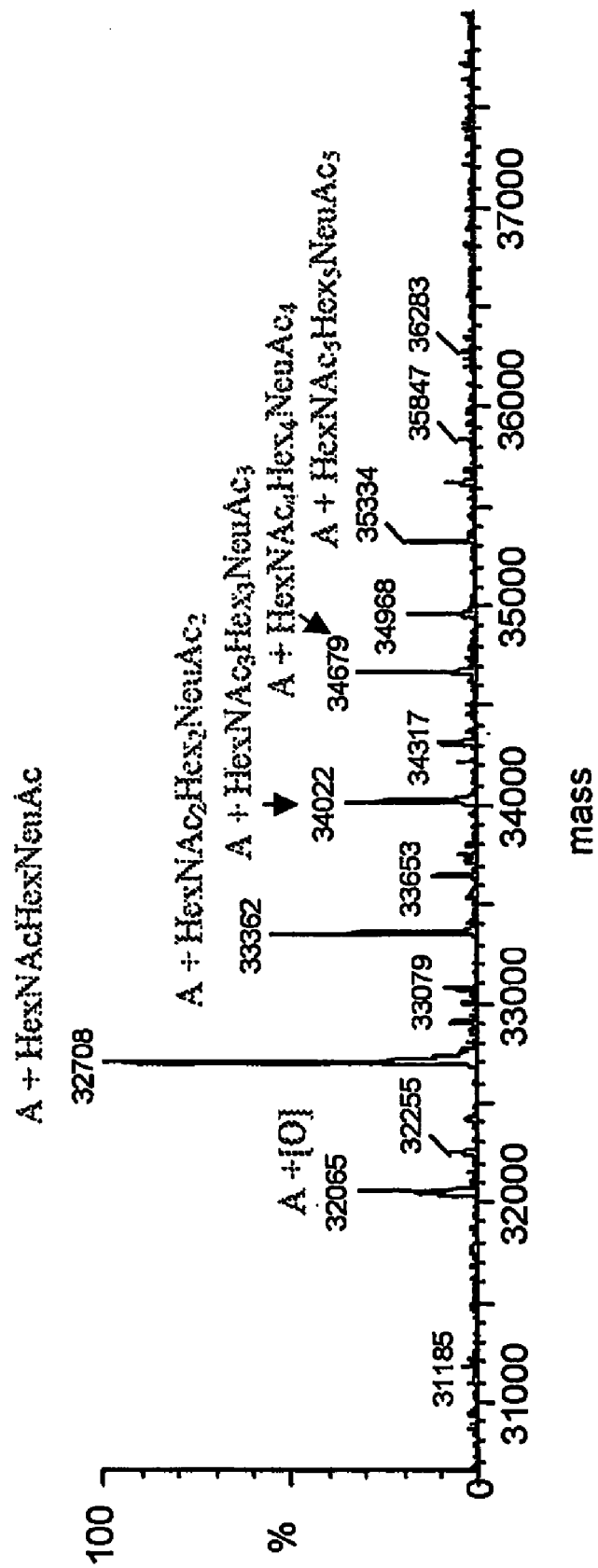
Figure 8G:
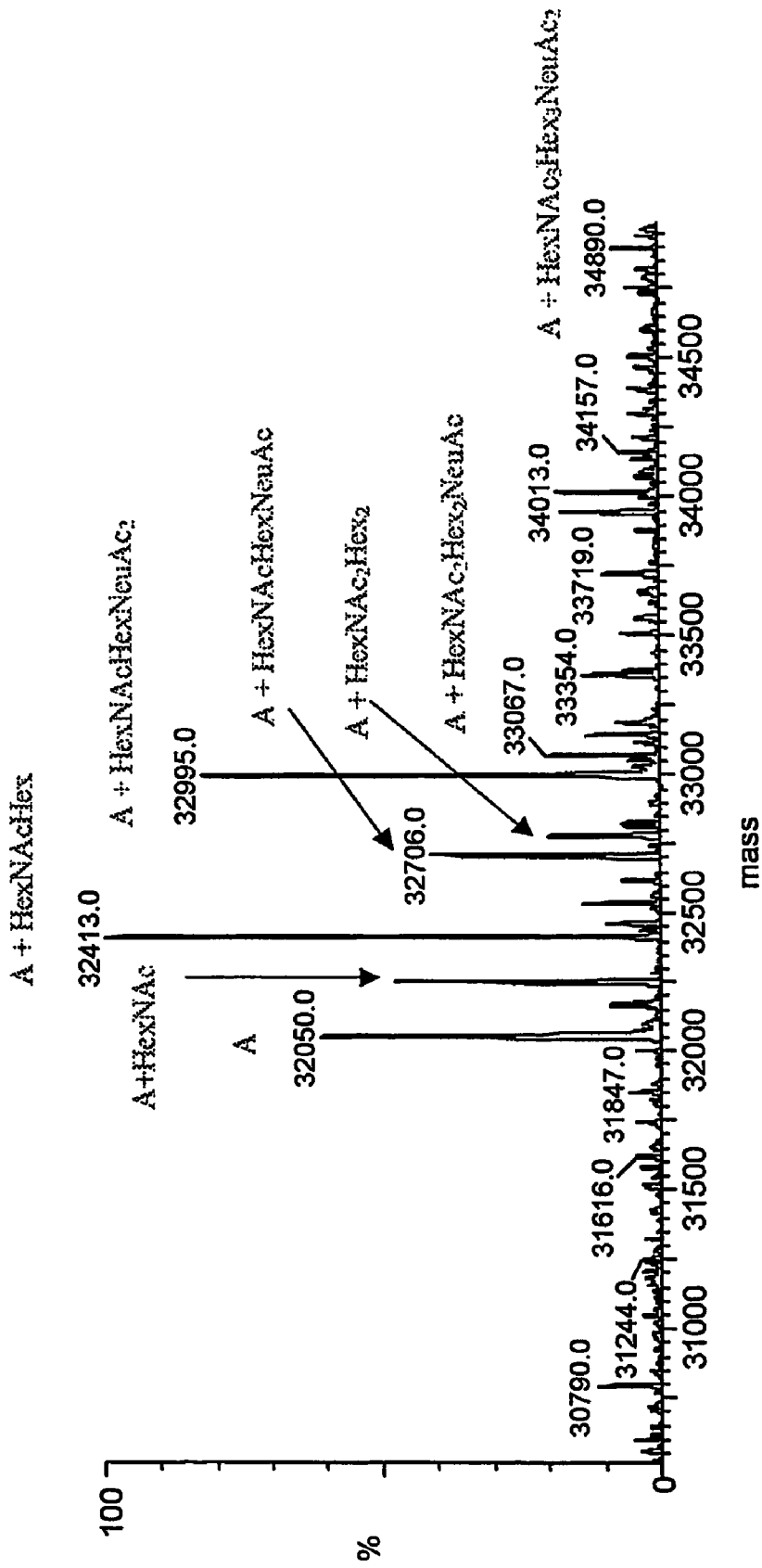
FIGS. 8G-8H show, respectively, mass spectra of vBAFF-R(R3-A72):Fc and mBAFF-R:Fc produced by 293EBNA cells, indicating molecular weights of the O-linked glycosylation forms associated with each peak.
Figure 8H:
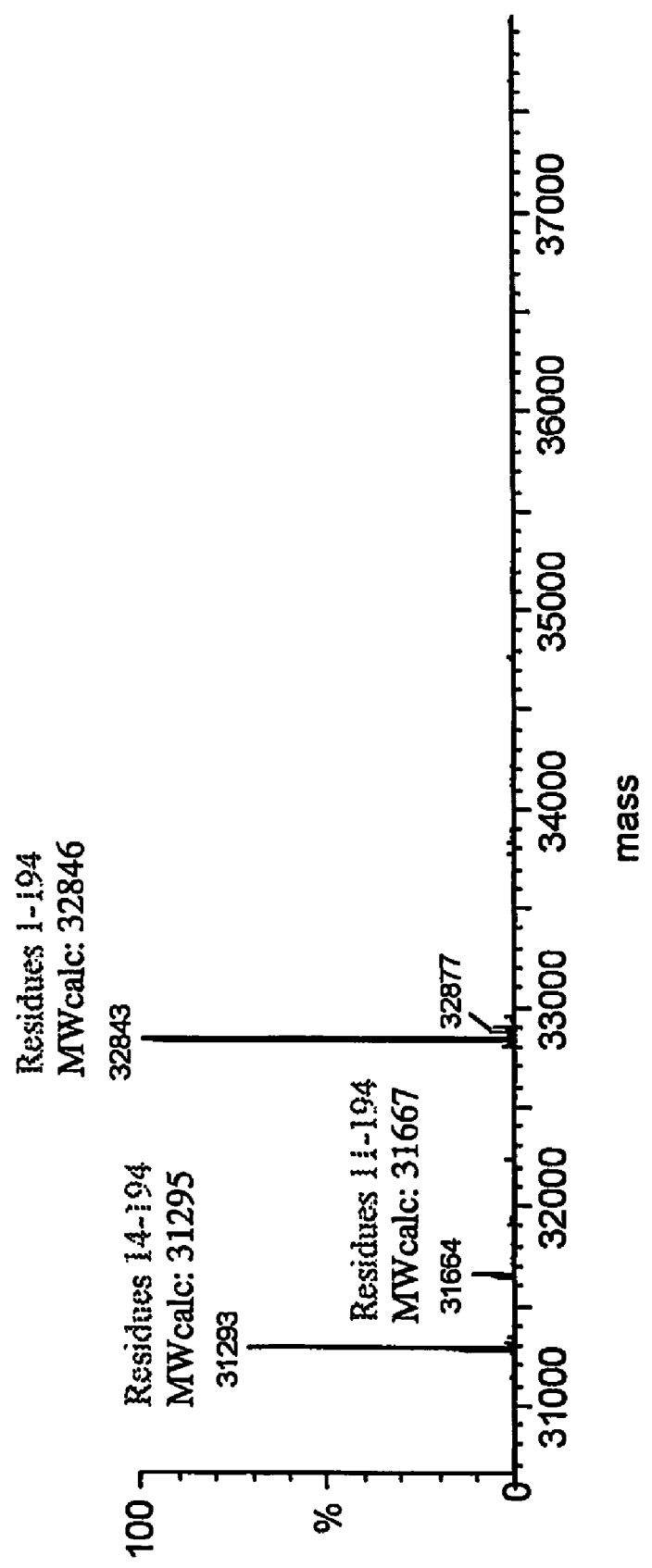

The detectable peaks in the mass spectrum in FIG. 7 show that there are numerous O-linked forms of the vBAFF-R(R3-A72):Fc protein. For each detectable peak, there are numerous different potential glycosylation patterns amongst the six potential O-linked glycosylation sites present in the molecule. The percent occupancy of some of these sites is shown in Table 2. FIGS. 8A-8H show the mass spectra for the vBAFF-R(R3-A72):Fc protein expressed in different CHO cell lines (FIGS. 8A-F) and a 293 cell line (FIG. 8G). FIG. 8H shows a mass spectrum for mBAFF-R:hFc.

Table 2 represents a summary of a series of experiments analyzing the glycosylation of specific potential glycosylation sites in vBAFF-R(R3-A72):Fc protein. The proximity of T41, S50, S51, T56, and S63 prevents the determination of which site is occupied. However, a proteolytic fragment containing these five sites has an 80% chance of being glycosylated, while a fragment containing just the T18 site is has only a 20-40% chance of being glycosylated. This unpredictability in the glycosylation pattern and the inability to determine the source of any given glycans creates problems for large-scale production of the protein.

TABLE 2

|  | \multicolumn{2}{c}{Recovery} |  | \multicolumn{3}{c}{O-linked Carbohydrates Occupancy} |
| --- | --- | --- | --- | --- | --- | --- |
| CHO clone | Post-PA | Post-buffer exchange | Productivity (mg/L) | Occupancy at T18 | at T41/S50/ S51/T56/S63 | Hydroxylated Pro-52 |
| 2-11 | 4.2 | 3 | 30 | 29% | 83% | 37% |
| 2-6 | 1.9 | 1 | 10 | 20% | 83% | 30% |
| 2-1 | 3.2 | 1.5 | 15 | 26% | 80% | 32% |
| 22 | 2.7 | 2.1 | 21 | 40% | 93% | 39% |

TABLE 2-continued

| | Recovery | | | Occupancy | | |
|---|---|---|---|---|---|---|
| CHO clone | Post-PA | Post-buffer exchange | Productivity (mg/L) | Occupancy at T18 | at T41/S50/ S51/T56/S63 | Hydroxylated Pro-52 |
| 18 | 3.4 | 2.6 | 26 | 35% | 94% | 31% |
| 7 | 3 | 1.6 | 16 | 31% | 91% | 32% |
| 52 | 2.2 | 1.7 | 17 | 28% | 87% | 30% |
| 60 | 1.7 | 1.6 | 16 | 26% | 83% | 30% |
| 3-1 | 2 | 1.8 | 18 | 28% | 88% | 27% |
| mBAFFR hFc 7068-44 | 18.2 | 18 | 15.1 | N/A | N/A | N/A |
| vBAFFR Fc 293 | N/A | N/A | N/A | 30–40% | 80–90% | N/A |

Figure 9:
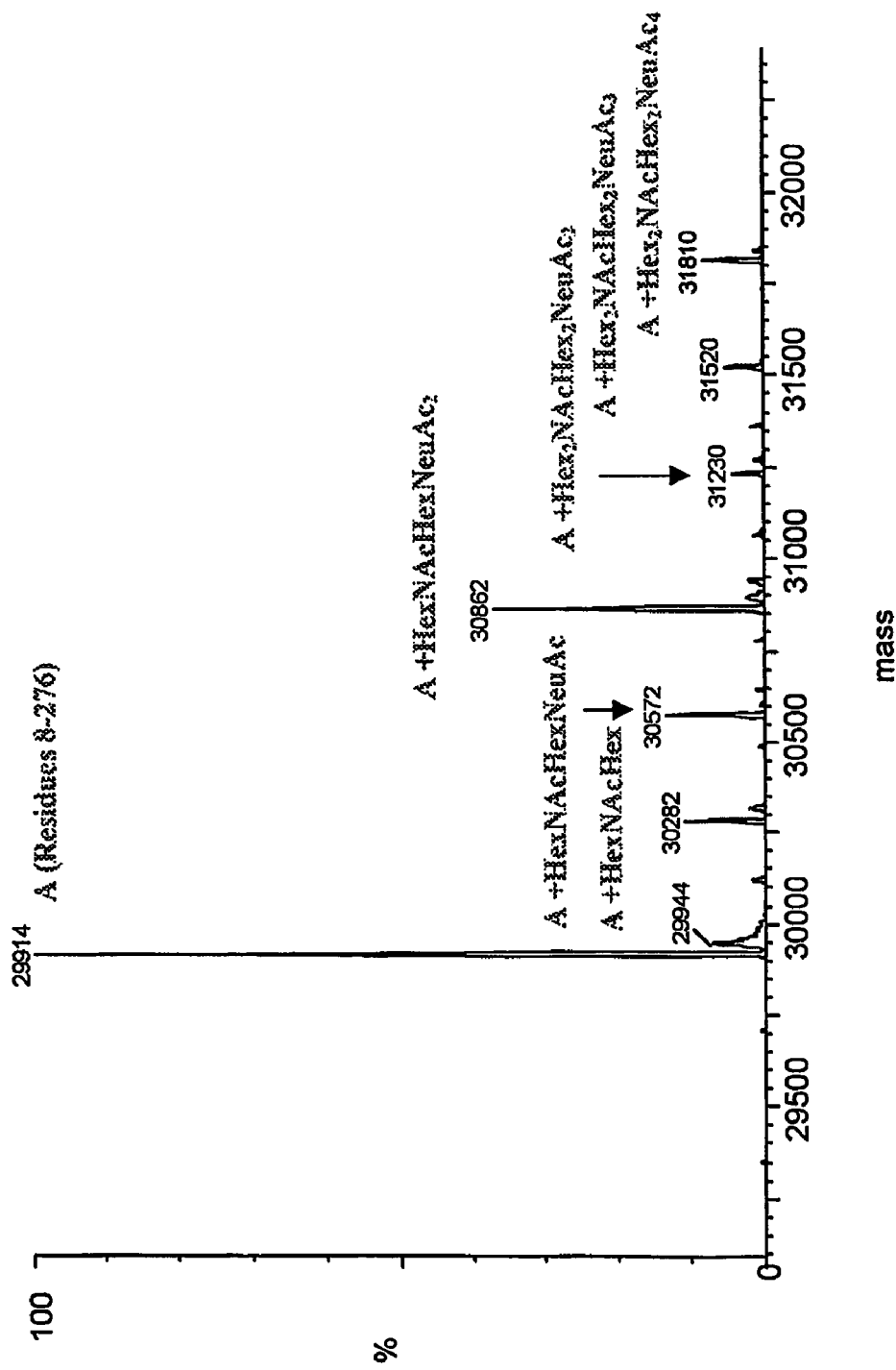
FIG. 9 shows a mass spectrum of vBAFF-R(R3-A49):Fc isolated from a CHO clone, indicating molecular weights of the O-linked glycosylation forms associated with each peak.

The mass spectrum of vBAFF-R(R3-A49) is shown in FIG. 9 and summarized in Table 3.

TABLE 3

| Detected mass | Probable assignment | Calculated mass (N-deglycosylated and reduced) |
|---|---|---|
| 29914 | Residues 8-276 (major component) | 29914 |
| 30572 | Residues 8-276 + (HexNAc)(Hex) | 30279 |
| 30572 | Residues 8-276 + (HexNAc)(Hex)(NeuAc) | 30571 |
| 30862 | Residues 8-276 + (HexNAc)(Hex)(NeuAc)$_2$ | 30862 |
| 31230 | Residues 8-276 + (HexNAc)$_2$(Hex)$_2$(NeuAc)$_2$ | 31227 |
| 31520 | Residues 8-276 + (HexNAc)$_2$(Hex)$_2$(NeuAc)$_3$ | 31519 |
| 31810 | Residues 8-276 + (HexNAc)$_2$(Hex)$_2$(NeuAc)$_4$ | 31810 |

The glycosylation pattern of vBAFF-R(R3-A49):Fc polypeptide is much simpler than full-length ECD BAFF-R, vBAFF-R(R3-A72):Fc. This shorter polypeptide contains only two potential O-linked glycosylation sites (T18 and T41). There are only seven peaks in this spectrum, each of which represents a small number of possible glycosylation patterns. For example, the 30572 peak represents a ΔBAFF-R:Fc protein with one core disaccharide (HexNAc)(Hex) linked to either T18 or T41. The most glycosylated species is the 31810 peak, in which each of the two core disaccharides are derivatized with the sialic acids (NeuAc). When compared to the full-length extracellular domain of BAFF-R, this altered glycosylation pattern allows for easier characterization of the variability between batches of pharmaceutical compositions comprising BAFF-R. Table 4 represents a summary of the analysis of glycosylation site occupancy and O-linked sugar profile of the two potential glycosylation sites in vBAFF-R(R3-A49):Fc (Thr-18 and Thr-41).

TABLE 4

| | | O-linked sugar profile | | | |
|---|---|---|---|---|---|
| Site | Total occupancy | HexNAc | HexNAc-Hex | HexNAc-Hex-NeuAc | HexNAc-Hex-(NeuAc)$_2$ |
| Thr-18 | 40% | 10% | 5% | 5% | 20% |
| Thr-41 | 70% | 0% | 10% | 20% | 40% |

EXAMPLE 7

Figure 10:
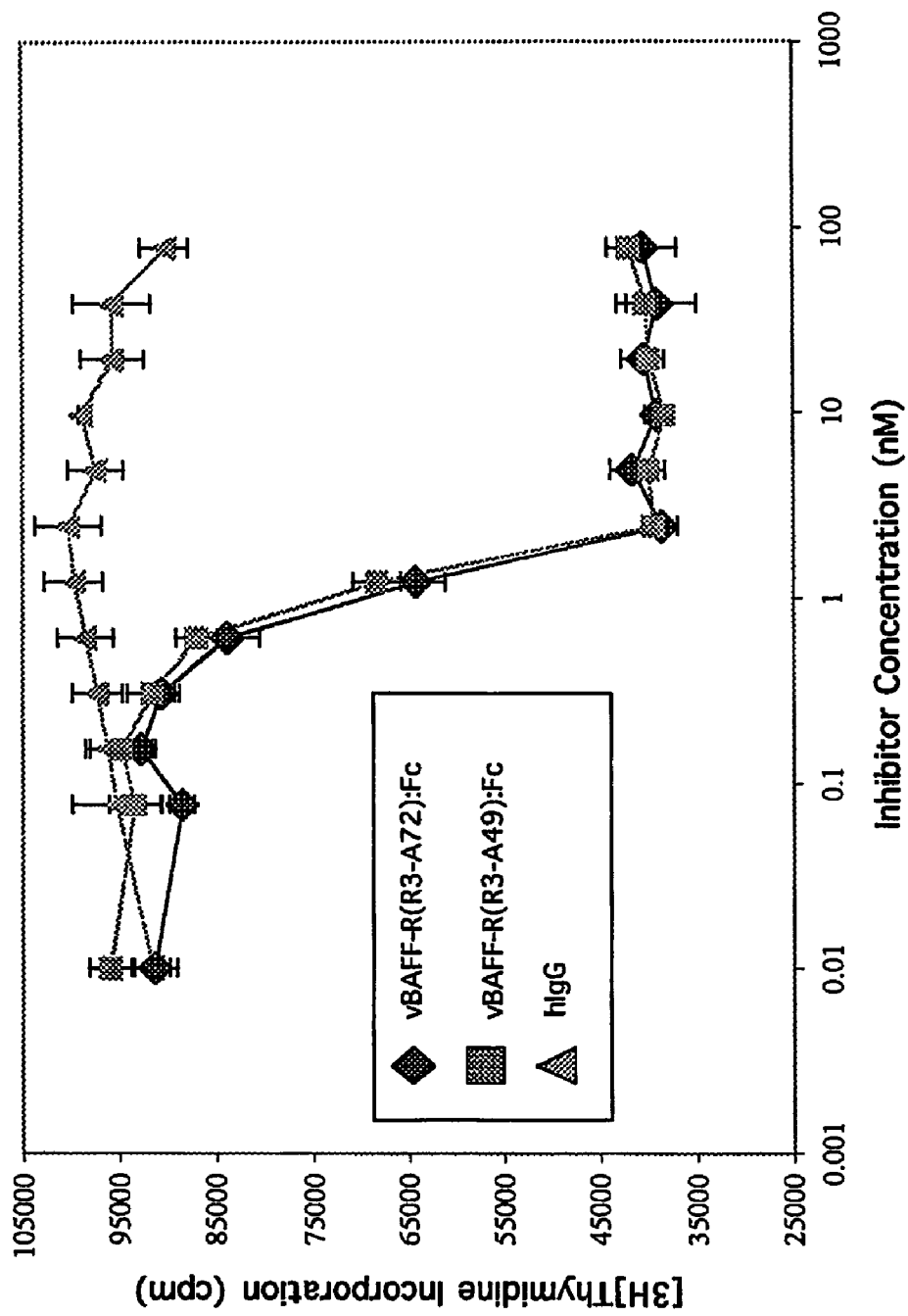
FIG. 10 shows the effect of increasing vBAFF-R(R3-A49):Fc concentration in the growth media on mouse splenic B cells' ability to incorporate [$^3$H]-thymidine. Triangles represent cultures treated with human IgG as the inhibitor, squares represent vBAFF-R(R3-A49):Fc treatment, and diamonds represent vBAFF-R(R3-A72):Fc treatment.

This example illustrates the ability of vBAFF-R(R3-A72) and vBAFF-R(R3-A49):Fc to inhibit the B cell survival activity of hBAFF on mouse splenic B cells. BAFF induced cell proliferation assay was performed using mouse splenic B cells. Mouse B cells were isolated from the spleens of two one month old C57/black6 mice using a B cell recovery column (Cedarlane Labs). B cells were incubated in flat-bottom 96-well plates ($10^5$ cells/well in 100 µl RPMI supplemented with 10% FBS) for 72 hours in the presence of 5 µg/ml of goat anti-mouse µ chain antibody (Jackson ImmunoResearch), 75 ng/ml of myc-hBAFF, and serial dilutions of vBAFF-R(R3-A49):Fc, vBAFF-R(R3-A72), or human IgG. Cells were pulsed for an additional 18 hours with [$^3$H]-thymidine (1 µCi/well) and harvested. [$^3$H]-thymidine incorporation was monitored by liquid scintillation counting. FIG. 10 shows that, in vitro, vBAFF-R(R3-A49):Fc, and vBAFF-R(R3-A72) inhibit BAFF-mediated B cell proliferation equally well, as demonstrated by reduced [$^3$H]-thymidine incorporation when compared to cells incubated with hIgG.

EXAMPLE 8

This example shows that in vivo BAFF blockade with vBAFF-R(R3-49):Fc impairs B cell survival, resulting in a reduction in the number of peripheral B cells, and causes a reduction in the level of expression of the B cell surface markers, CD21 and CD23.

A total of 37 female BALB/c mice were assigned to 8 treatment groups as shown in Table 5. All animals were dosed with 200 µl of vBAFF-R(R3-49):Fc or hIgG intraperoneally (10 ml/kg dose volume). 96 hours post-dose mice were euthanized and spleens were harvested for quantitation of B cells.

TABLE 5

| Group | Test article | Number of animals in group | Dose level (mg/kg) |
|---|---|---|---|
| 5 | Truncated vBAFF-R:Fc | 3 | 0.05 |
| 6 | | 3 | 0.25 |
| 7 | | 4 | 0.5 |
| 8 | | 3 | 5 |
| 9 | Human IgG (hIgG) | 3 | 0.05 |
| 10 | | 3 | 0.25 |
| 11 | | 2 | 0.5 |
| 12 | | 3 | 5 |

Splenocytes were prepared by mechanical disruption. Debris was eliminated by passing through a 100 μm cell strainer. Red cells were lysed in 5 ml of ACK solution (155 mM ammonium chloride, 10 mM potassium bicarbonate, 0.1 mM EDTA, pH 7.3), then washed 3 times in 10 ml PBS and suspended in FACS buffer (0.5% FBS, 0.01 sodium azide). Debris was eliminated by passing through a 100 μm cell strainer, and viable cells were counted using trypan blue exclusion.

FACS staining: 2 million cells were stained/sample in a volume of 100 μl. Cells were incubated on ice with Block buffer (FACS™ buffer with 10 μg/ml Fc Block, 5% rat serum) to prevent FcgR (Fc gamma receptor) on splenocytes from interacting with the Fc domain of the mAbs, thereby minimizing background staining. Specific cocktails of mAbs were added and incubated on ice for 30 minutes. Cells were washed with FACS™ buffer, then suspended in FACS™ buffer containing streptavidin-PerCP (Streptavidin-Peridinin chlorophyll-a Protein, a fluorescent tagged streptavidin used to detect the biotin-CD23 probe) and incubated on ice for 30 minutes. Cells were washed in FACS buffer and suspended in 150 μl 0.5% paraformaldehyde in PBS for analysis in a FACSCaliber™ flowcytometer. 100,000 events were collected, and analysis was done using CellQuest™ software. Statistical analysis was performed using Student's t test.

Figure 11:
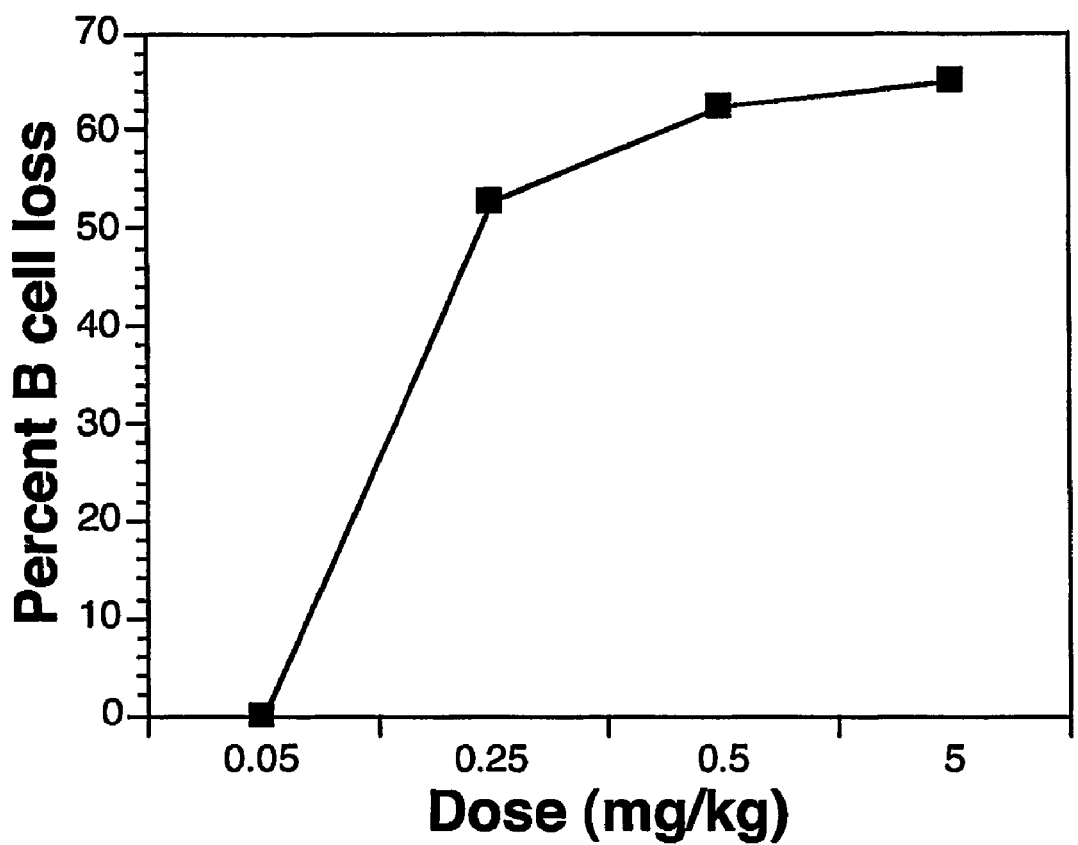
FIG. 11 shows the effect of vBAFF-R(R3-A49):Fc on the number of CD19+ splenic B cells.

The numbers of splenic B cells were calculated based on total splenocyte number and percent of CD19+cells. As seen in FIG. 11, vBAFF-R(R3-49):Fc-treated mice exhibited a marked loss of splenic B cells when compared to controls. B cell loss was observed with a dose as low as 0.25 mg/kg, and the percent loss increased with higher doses of vBAFF-R(R3-49): Fc.

The impact of BAFF inhibition with vBAFF-R(R3-49):Fc on splenic mature ($IgM^{lo}IgD^{hi}$) and marginal zone (MZ) ($IgM^{hi}IgD^{lo}$) B cell CD21 and CD23 expression was examined. CD21 mean fluorescence intensity (MFI) was significantly diminished on all B cell subsets examined in the 0.25, 0.5, and 5 mg/kg dose groups that received vBAFF-R(R3-49):Fc, when compared to hIgG-treated controls (Table 6).

TABLE 6

| Dose (mg/kg) | Treatment | Mature B[a] | MZ B[a] |
|---|---|---|---|
| 5 | hIgG | 28.5 ± 3.4[b] | 97.4 ± 10.2 |
|  | vBAFF-R:Fc | 12.5 ± 0.9* | 69.3 ± 10* |
| 0.5 | hIgG | 28.7 ± 0.6 | 84 ± 0.6 |
|  | vBAFF-R:Fc | 17.6 ± 0.9* | 66 ± 3.7* |
| 0.25 | hIgG | 25.5 ± 0.3 | 91.2 ± 3.1 |
|  | vBAFF-R:Fc | 20 ± 1.4* | 76 ± 5.1 |
| 0.05 | IgG | 31.8 ± 1.5 | 90.1 ± 1.8 |
|  | vBAFF-R:Fc | 31.9 ± 0.7 | 87.4 ± 3.9 |

[a]Cells obtained from spleens for FACS ™ analysis
[b]Mean fluorescence intensity ± standard deviation
*$p < 0.05$ CD23 expression was significantly reduced on mature and MZ B cells from vBAFF-R(R3-49):Fc-treated mice when compared hIgG-treated controls at the 5 mg/kg dose (Table 7).

TABLE 7

| Dose (mg/kg) | Treatment | Mature B[a] | MZ B[a] |
|---|---|---|---|
| 5 | hIgG | 105.1 ± 18[b] | 29.2 ± 0.6 |
|  | vBAFF-R:Fc | 64.3 ± 4.5* | 18.2 ± 2.1* |
| 0.5 | hIgG | 211.1 ± 3.8 | 51.7 ± 5 |
|  | vBAFF-R:Fc | 201 ± 12.9 | 41.1 ± 0.9 |

TABLE 7-continued

| Dose (mg/kg) | Treatment | Mature B[a] | MZ B[a] |
|---|---|---|---|
| 0.25 | hIgG | 199 ± 7.1 | 60.2 ± 3.1 |
|  | vBAFF-R:Fc | 195.9 ± 11.4 | 52.3 ± 5.3 |
| 0.05 | IgG | 175.5 ± 8.8 | 77 ± 9.6 |
|  | vBAFF-R:Fc | 173.2 ± 9.9 | 62.6 ± 5.7 |

[a]Cells obtained from spleens for FACS ™ analysis
[b]Mean fluorescence intensity ± standard deviation
*$p < 0.05$

EXAMPLE 9

This examples illustrates the binding between flag-huBAFF and vBAFF-R(R3-A49):Fc or vBAFF-R(R3-A72):Fc in two ELISA formats. ELISA plates were coated with a capture antibody at 50 μl/well at 5 μg/ml in 50 mM sodium bicarbonate pH 9.6 overnight at 4° C. Capture antibodies were anti-human IgG Fc (Jackson ImmunoResearch) or M2 anti-FLAG (Sigma). Plates were blocked with 3% BSA in PBS at room temperature (RT) for 30 minutes and washed 3 times with 250 μl of PBS+0.05% Tween 20™. All subsequent incubations were at RT with reagents diluted in 3% BSA-PBS.

Figure 12:
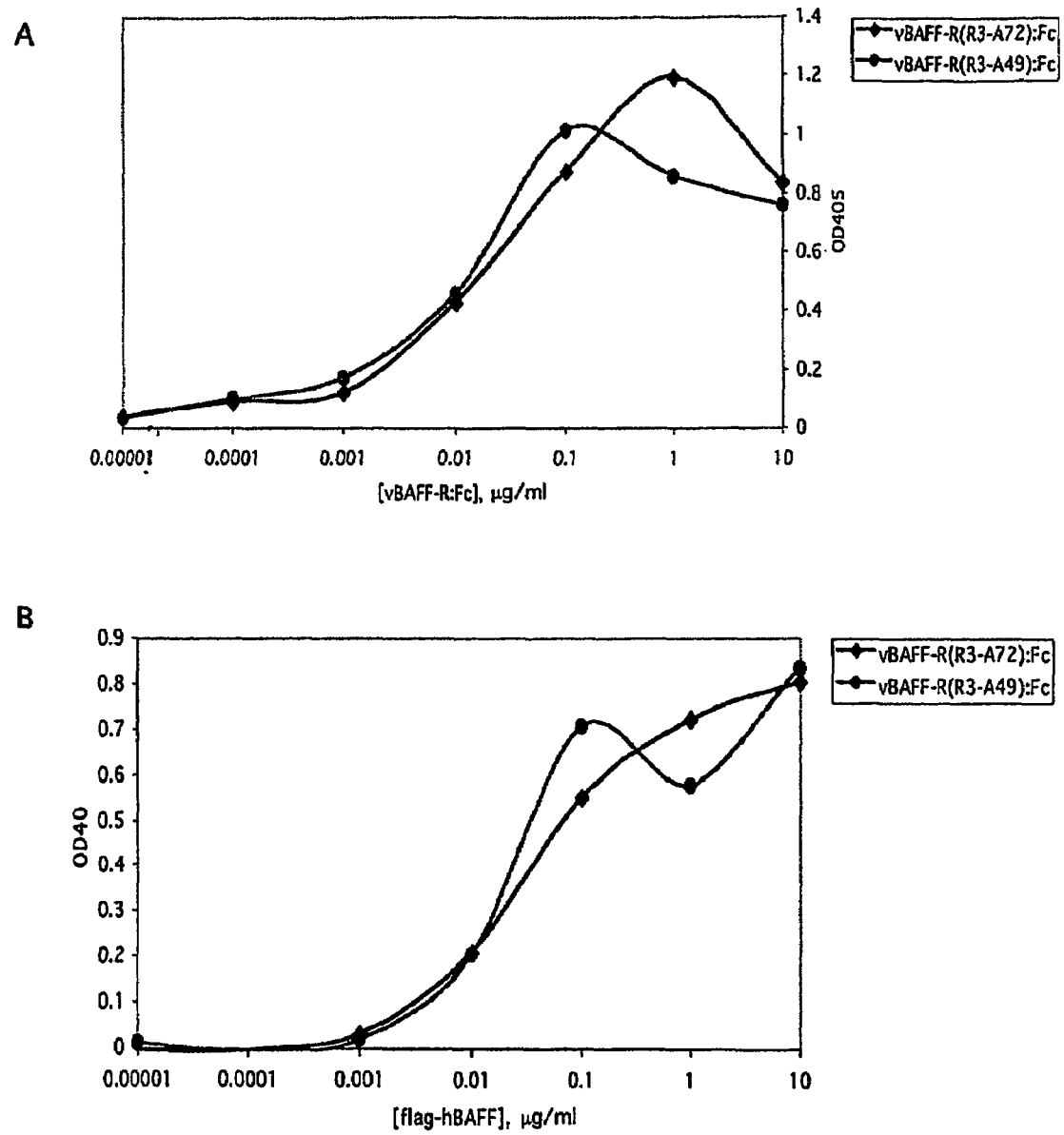
FIG. 12A shows results of an ELISA capture experiment in which hBAFF was immobilized and the binding affinities of vBAFF-R(R3-A49):Fc and vBAFF-R(R3-A72):Fc to BAFF were measured by OD405.
FIG. 12B shows results of a similar ELISA experiment in which vBAFF-R(R3-A49):Fc and vBAFF-R(R3-A72):Fc were immobilized and the binding of FLAG-hBAFF was measured by OD405.

On the anti-human IgG Fc coated plate, 50 μl of vBAFF-R(R3-A49):Fc or vBAFF-R(R3-A72):Fc were captured at 2 μg/ml for 2 hours and then washed as above (FIG. 12A). Ten-fold serial dilutions starting at 10 μg/ml of 50 μl of FLAG-huBAFF were added, incubated for 30 minutes and washed. M2 anti-FLAG at 1 μg/ml, 100 μl, was added for 30 minutes and washed. A 1:3000 dilution of ant-murine IgG alkaline phosphatase conjugate (Jackson ImmunoResearch), 100 μl, for 30 minutes.

On the anti-FLAG coated plate, 50 μl of 10 μg/ml FLAG-huBAFF was added and incubated for 2 hours and washed as above (FIG. 12B). Ten-fold serial dilutions starting at 10 μg/ml of 50 μl of vBAFF-R(R3-A49):Fc and vBAFF-R(R3-A72):Fc were added and incubated for 30 minutes and washed as above. A 1:3000 dilution of anti-human Fc gamma alkaline phosphatase conjugate (Jackson ImmunoResearch) (1:3000 dilution), 100 μl, for 30 minutes.

After washing, detection for both sets of plates was achieved by incubation with 100 μl of 2 mg/ml pNpp (Pierce) in 10% diethanolamine pH9.0, 1 mM $MgCl_2$, 1 mM $ZnCl_2$ at room temperature until sufficient color formation was observed. $OD_{405}$ was read.

As shown in FIGS. 12A and 12B, under both ELISA formats, the IC50 for ligand binding for vBAFF-R(R3-A49):Fc and vBAFF-R(R3-A72):Fc show the same high functional affinity for FLAG-huBAFF, regardless if ligand or receptor Fc fusion is in solution.

The specification is most thoroughly understood in light of the teachings of the references cited within the specification, which are hereby incorporated by reference. The embodiments within the specification provide an illustration of embodiments of the invention and should not be construed to limit the scope of the invention. The skilled artisan readily recognizes that many other embodiments are encompassed by the invention. All publications and patents cited and sequences identified by accession or database reference numbers in this disclosure are incorporated by reference in their entirety. To the extent the material incorporated by reference contradicts or is inconsistent with the present specification, the present specification will supersede any such material.

The citation of any references herein is as not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention claimed is:

1. A glycoprotein comprising the extracellular domain of a non-naturally occurring BAFF-R (BAFF receptor), wherein the extracellular domain of the non-naturally occurring BAFF-R has a deletion that results in an altered O-linked glycosylation pattern, and wherein the non-naturally occurring BAFF-R retains the ability to bind to BAFF (B-cell-activating factor of the TNF family).

2. The glycoprotein of claim 1, wherein the extracellular domain of the non-naturally occurring BAFF-R has at least one O-linked glycan.

3. The glycoprotein of claim 2, wherein the O-linked glycan is attached on an amino acid that corresponds to threonine 18 or threonine 41 of SEQ ID NO:1.

4. The glycoprotein of claim 2, wherein the O-linked glycan is attached on an amino acid which corresponds to threonine 18, threonine 41, or serine 8 of SEQ ID NO:1.

5. The glycoprotein of claim 1, wherein the extracellular domain of the non-naturally occurring BAFF-R comprises amino acids 14 to 43 of SEQ ID NO:1.

6. The glycoprotein of claim 5, wherein the deletion corresponds to amino acid 50 to amino acid 56 of SEQ ID NO:1.

7. The glycoprotein of claim 5, wherein the deletion corresponds to amino acid 50 to amino acid 63 of SEQ ID NO:1.

8. The glycoprotein of claim 5, wherein the deletion corresponds to amino acid 50 to amino acid 72 of SEQ ID NO:1.

9. The glycoprotein of claim 1, wherein the extracellular domain of the non-naturally occurring BAFF-R comprises an amino acid sequence substantially identical to SEQ ID NO:1 from amino acid 13 to amino acid 43.

10. The glycoprotein of claim 1, wherein the extracellular domain of the non-naturally occurring BAFF-R comprises an amino acid sequence substantially identical to SEQ ID NO:1 from amino acid 14 to amino acid 43.

11. The glycoprotein of claim 5, having at least two amino acid substitutions, wherein the substituted amino acids correspond to amino acid positions 21 and 28 of SEQ ID NO:1.

12. The glycoprotein of claim 1, wherein the extracellular domain of the non-naturally occurring BAFF-R glycoprotein consists of an amino acid sequence selected from the group consisting of:
  (a) amino acids 13 to 43 of SEQ ID NO:1;
  (b) amino acids 14 to 43 of SEQ ID NO:1;
  (c) amino acids 1 to 49 of SEQ ID NO:1;
  (d) amino acids 13 to 49 of SEQ ID NO:1;
  (e) amino acids 14 to 49 of SEQ ID NO:1; and
  (f) amino acids 1 to 49 of SEQ ID NO:7.

13. The glycoprotein of claim 1, wherein the extracellular domain of the non-naturally occurring BAFF-R comprises an amino acid sequence from amino acid 1, 2, 3, 4, 5, 6, 7, 8, 9, 10, 11, 12, 13, 14, 15, 16, 17, 18, or 19 of SEQ ID NO:1 to amino acid 43, 44, 45, 46, 47, 48, or 49 of SEQ ID NO:1.

14. The glycoprotein of claim 13, wherein the amino acid corresponding to position 21 of SEQ ID NO:1 is valine and the amino acid corresponding to position 28 of SEQ ID NO:1 is leucine.

15. The glycoprotein of claim 13, wherein the amino acid corresponding to position 21 of SEQ ID NO:1 is substituted with asparagine and the amino acid corresponding to position 28 of SEQ ID NO:1 is substituted with proline.

16. The glycoprotein of claim 13, further comprising at least a portion of an immunoglobulin constant region, and optionally a linker joining the amino acid sequence to said portion of an immunoglobulin constant region, wherein the linker does not include amino acids 50 to 56 of SEQ ID NO:1.

17. The glycoprotein of claim 16, wherein the portion of the immunoglobulin is IgG1 or Ig4.

18. The glycoprotein of claim 17, wherein the portion of the immunoglobulin constant region comprises amino acids 3 to 227 of SEQ ID NO:4.

19. A nucleic acid encoding the glycoprotein of claim 1.

20. The nucleic acid of claim 19, wherein the encoded glycoprotein comprises an amino acid sequence selected from the group consisting of:
  (a) amino acids 13 to 43 of SEQ ID NO:1;
  (b) amino acids 14 to 43 of SEQ ID NO:1
  (c) amino acids 1 to 49 of SEQ ID NO:1;
  (d) amino acids 8 to 49 of SEQ ID NO:1;
  (e) amino acids 13 to 49 of SEQ ID NO:1;
  (f) amino acids 14 to 49 of SEQ ID NO:1; and
  (g) amino acids 1 to 49 of SEQ ID NO:7.

21. The nucleic acid of claim 19, comprising nucleotides 1 to 216 of SEQ ID NO:2 or 3.

22. A vector comprising the nucleic acid of any one of claims 19 to 21.

23. An isolated host cell comprising the nucleic acid of any one of claims 19 to 21.

24. A method for producing a glycoprotein, the method comprising the steps of:
  (a) transforming isolated host cells with the vector of claim 22;
  (b) culturing the host cells under conditions permitting production of the glycoprotein; and
  (c) isolating the glycoprotein from the host cells.

25. A BAFF-R fusion polypeptide comprising:
  (a) a first amino acid sequence selected from the group consisting of
    (i) amino acids 13 to 43 of SEQ ID NO:1;
    (ii) amino acids 14 to 43 of SEQ ID NO:1;
    (iii) amino acids 1 to 49 of SEQ ID NO:1;
    (iv) amino acids 13 to 49 of SEQ ID NO:1;
    (v) amino acids 14 to 49 of SEQ ID NO:1; and
    (vi) amino acids 1 to 49 of SEQ ID NO:7; fused to
  (b) a second amino acid sequence comprising at least a portion of an immunoglobulin constant region, and optionally
  (c) a linker joining the first and the second amino acid sequences,
  wherein the BAFF-R fusion polypeptide does not include amino acid 50 to amino acid 56 of SEQ ID NO:1.

26. The BAFF-R fusion polypeptide of claim 25, wherein the linker is proteinaceous.

27. The BAFF-R fusion polypeptide of claim 25, wherein the first amino acid sequence comprises amino acids 8 to 49 of SEQ ID NO:1.

28. The BAFF-R fusion polypeptide of claim 25, wherein the first amino acid sequence comprises amino acids 13 to 43 of SEQ ID NO:1.

29. The BAFF-R fusion polypeptide of claim 25, wherein the first amino acid sequence comprises amino acids 14 to 43 of SEQ ID NO:1.

30. A BAFF-R fusion polypeptide comprising: (a) a first amino acid sequence comprising amino acids 14 to 43 of SEQ ID NO:1 modified by amino acid substitutions at positions 21 and 28 of SEQ ID NO:1, fused to (b) a second amino acid sequence comprising at least a portion of an immunoglobulin constant region, and optionally (c) a linker joining the first and second amino acid sequences, wherein the BAFF-R fusion polypeptide does not include amino acids 50 to 56 of SEQ ID NO:1.

31. The BAFF-R fusion polypeptide of claim 25, wherein the first amino acid sequence comprises amino acid 1, 2, 3, 4, 5, 6, 7, 8, 9, 10, 11, 12, 13, 14, 15, 16, 17, 18, or 19 of SEQ ID NO:1 to amino acid 43, 44, 45, 46, 47, 48, or 49 of SEQ ID NO:1 and the second amino acid sequence comprises amino acids 3 to 227 of SEQ ID NO:4.

32. A nucleic acid encoding the BAFF-R fusion polypeptide of claim 25.

33. The nucleic acid of claim 32, comprising nucleotides encoding amino acids 1-227 of SEQ ID NO:4 fused to an amino acid sequence selected from the group consisting of:
    (a) amino acids 13 to 43 of SEQ ID NO:1;
    (b) amino acids 14 to 43 of SEQ ID NO:1;
    (c) amino acids 1 to 49 of SEQ ID NO:1;
    (d) amino acids 13 to 49 of SEQ ID NO:1;
    (e) amino acids 14 to 49 of SEQ ID NO:1; and
    (f) amino acids 1 to 49 of SEQ ID NO:7.

34. The nucleic acid of claim 32, comprising (a) nucleotides 1 to 216 of SEQ ID NO:2 or SEQ ID NO:3 and (b) nucleotides 7 to 681 of SEQ ID NO:5.

35. A vector comprising the nucleic acids of any one of claims 32-34.

36. An isolated host cell comprising the nucleic acid of any one of claims 32-34.

37. A pharmaceutical composition comprising the glycoprotein of claim 1.

38. A pharmaceutical composition comprising the BAFF-R fusion polypeptide of claim 25.

39. A method for treating a patient having an autoimmune disease characterized by elevated levels of BAFF comprising administering a therapeutically effective amount of the pharmaceutical composition of claim 37 or claim 38 to the patient.

40. The glycoprotein of claim 1, having an apparent affinity for BAFF in the nanomolar range.

41. The BAFF-R fusion polypeptide of claim 25, having an apparent affinity for BAFF of at least $10^9$ M$^{-1}$.

42. A method for treating a patient having rheumatoid arthritis comprising administering a therapeutically effective amount of the pharmaceutical composition of claim 37 or claim 38 to the patient.

43. A method for treating a patient having systemic lupus erythematosis comprising administering a therapeutically effective amount of the pharmaceutical composition of claim 37 or claim 38 to the patient.

\* \* \* \* \*

UNITED STATES PATENT AND TRADEMARK OFFICE
CERTIFICATE OF CORRECTION

PATENT NO. : 7,700,317 B2  Page 1 of 1
APPLICATION NO. : 10/550961
DATED : April 20, 2010
INVENTOR(S) : Ambrose et al.

It is certified that error appears in the above-identified patent and that said Letters Patent is hereby corrected as shown below:

Title page 1 of the patent, item (73):

"Biogen Idec Ma Inc." should read --Biogen Idec MA Inc.--

Signed and Sealed this

Twenty-second Day of June, 2010

David J. Kappos
*Director of the United States Patent and Trademark Office*